(12) United States Patent
Kouyoumjian et al.

(10) Patent No.: US 9,072,839 B2
(45) Date of Patent: Jul. 7, 2015

(54) AUTOMATIC DELIVERY DEVICE WITH TRIGGERING MECHANISM

(75) Inventors: Garen Kouyoumjian, Warwickshire (GB); Malcolm Stanley Boyd, Warwickshire (GB); Daniel Thomas De Sausmarez Lintell, Warwickshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 5 days.

(21) Appl. No.: 13/988,593

(22) PCT Filed: Nov. 28, 2011

(86) PCT No.: PCT/EP2011/071146
§ 371 (c)(1),
(2), (4) Date: May 21, 2013

(87) PCT Pub. No.: WO2012/072568
PCT Pub. Date: Jun. 7, 2012

(65) Prior Publication Data
US 2013/0245562 A1      Sep. 19, 2013

Related U.S. Application Data

(60) Provisional application No. 61/433,819, filed on Jan. 18, 2011.

(30) Foreign Application Priority Data

Nov. 29, 2010   (EP) ..................................... 10192998

(51) Int. Cl.
*A61M 31/00* (2006.01)
*A61M 5/315* (2006.01)
*A61M 5/20* (2006.01)
*A61M 5/24* (2006.01)
*A61M 5/32* (2006.01)
*A61M 5/34* (2006.01)
*A61M 5/178* (2006.01)

(52) U.S. Cl.
CPC ............. *A61M 5/31596* (2013.01); *A61M 5/20* (2013.01); *A61M 5/2033* (2013.01); *A61M 5/2448* (2013.01); *A61M 5/2466* (2013.01); *A61M 5/31543* (2013.01); *A61M 5/31553* (2013.01); *A61M 5/31583* (2013.01); *A61M 5/326* (2013.01); *A61M 5/3272* (2013.01); *A61M 5/3294* (2013.01); *A61M 5/347* (2013.01); *A61M 2005/1787* (2013.01); *A61M 2005/2013* (2013.01); *A61M 2005/247* (2013.01); *A61M 2005/2474* (2013.01); *A61M 2005/3247* (2013.01); *A61M 2005/3267* (2013.01); *A61M 2205/6045* (2013.01)

(58) Field of Classification Search
CPC ... A61M 5/158; A61M 5/16827; A61M 5/19; A61M 5/3134; A61M 5/32; A61M 5/3202; A61M 5/321; A61M 5/3294; A61M 5/2448; A61M 5/3243; A61M 5/3269; A61M 5/3271; A61M 5/3272; A61M 5/3276; A61M 2005/1787; A61M 2005/208; A61M 2005/2448; A61M 2005/3236; A61M 2005/3263; A61M 5/20; A61M 5/2033; A61M 5/2466; A61M 5/31543; A61M 5/31553; A61M 5/31583; A61M 5/31596; A61M 5/326; A61M 5/347; A61M 2005/2013; A61M 2005/247; A61M 2005/2474; A61M 2005/3247; A61M 2005/3267; A61M 2205/6045; A61M 5/2066; A61M 5/284; A61M 5/31511; A61M 5/31533; A61M 5/31548; A61M 5/3155; A61M 5/31578; A61M 5/3257; A61M 2005/2006
USPC ........ 604/93.01, 82, 110, 134, 135, 136, 137, 604/138, 139, 181, 187, 192, 193, 194, 195, 604/196, 197, 198, 228, 232, 234, 264, 272, 604/87, 88, 191, 201
See application file for complete search history.

(56) References Cited

U.S. PATENT DOCUMENTS

| | | | |
|---|---|---|---|
| 3,797,491 A * | 3/1974 | Hurschman | 604/511 |
| 5,104,380 A | 4/1992 | Holman et al. | |
| 5,637,087 A * | 6/1997 | O'Neil et al. | 604/82 |
| 6,562,002 B1 | 5/2003 | Taylor | |
| 2002/0004648 A1 * | 1/2002 | Larsen et al. | 604/195 |
| 2005/0165363 A1 * | 7/2005 | Judson et al. | 604/209 |
| 2006/0276755 A1 | 12/2006 | Sullivan et al. | |
| 2007/0100288 A1 * | 5/2007 | Bozeman et al. | 604/181 |
| 2008/0147005 A1 * | 6/2008 | Moller et al. | 604/134 |
| 2009/0292240 A1 * | 11/2009 | KraMer et al. | 604/82 |
| 2010/0198151 A1 * | 8/2010 | Koyama et al. | 604/110 |

FOREIGN PATENT DOCUMENTS

| | | | |
|---|---|---|---|
| EP | 1728529 A1 | 12/2006 | |
| WO | 0176665 A1 | 10/2001 | |
| WO | 2010115670 A1 | 10/2010 | |

OTHER PUBLICATIONS

International Preliminary Report on Patentability for PCT/EP2011/071146 dated Jun. 13, 2013.

Machine Translation of WO 01/76665.

\* cited by examiner

*Primary Examiner* — Bhisma Mehta
*Assistant Examiner* — Nicholas Meghri
(74) *Attorney, Agent, or Firm* — McDonnell Boehnen Hulbert & & Berghoff LLP

(57) ABSTRACT

The present patent application relates to delivery devices, methods, and systems of delivering at least one medicament from a reservoir using an automatic delivery device. Such an automatic delivery device system may comprise a dose injecting mechanism and a dispense interface, such as a needle module. The dose injecting mechanism comprises a triggering mechanism. An activating member, such as a needle guard of the needle module, can be used to initiate the triggering mechanism to enable the device to administer the set dose. The single dispense interface may comprise a medicated module containing at least one dose of a secondary medicament. The dose injecting mechanism may comprise a dose setting mechanism.

13 Claims, 12 Drawing Sheets

AUTOMATIC DELIVERY DEVICE WITH TRIGGERING MECHANISM

CROSS REFERENCE TO RELATED APPLICATIONS

The present application is a U.S. National Phase application pursuant to 35 U.S.C. §371 of International Application No. PCT/EP2011/071146 filed Nov. 28, 2011, which claims priority to European Patent Application No. 10192998.2 filed Nov. 29, 2010 and U.S. Provisional Patent Application No. 61/433,819 filed Jan. 18, 2011. The entire disclosure contents of these applications are herewith incorporated by reference into the present application.

FIELD OF INVENTION

The present patent application relates to delivery devices, methods, and systems of delivering at least one medicament from a reservoir using an automatic delivery device. Such an automatic delivery device system may comprises a dose injecting mechanism and a dispense interface, such as a needle module. The dose injecting mechanism comprises an integrated triggering mechanism. An activating member, such as a needle guard of the dispense interface, can be used to initiate the triggering mechanism of the delivery device and enable the device to administer a dose of the primary medicament. An automatic delivery device may utilize energy stored within the delivery device to administer the dose automatically once the triggering mechanism has been activated.

In one arrangement, the dose injecting mechanism comprises a dose setting mechanism: a mechanism that allows a user to select or set a dose of the primary medicament contained within the delivery device. In another arrangement, the dose injecting mechanism comprises a single use device and a device that does not allow a user to set the dose. Rather, the dose is preset and the delivery device comprises a single use device. In one arrangement, the single dispense interface may comprise a medicated module containing at least one dose of a secondary medicament.

In another aspect of the present invention, a needle module may comprise a dedicated needle module. With such a dedicated needle module, the needle module may be mechanically configured so as to only properly connect to an associated dedicated delivery device, such as a dedicated pen type drug delivery device. Alternatively, the needle module may comprise a dedicated medicated module wherein the dedicated medicated module contains at least one dose of a secondary medicament and the dedicated medicate module is configured to only be used with a dedicated drug delivery device.

BACKGROUND

Certain disease states require treatment using one or more different medicaments. Some drug compounds need to be delivered in a specific relationship with each other in order to deliver the optimum therapeutic dose. One aspect of the present invention is of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems that can arise when delivering two medicaments or active agents simultaneously. The two active agents may interact with each other during the long-term, shelf life storage of the formulation. Therefore, it is advantageous to store the active components separately and only combine them at the point of delivery, e.g. injection, needle-less injection, pumps, or inhalation. However, the process for combining the two agents needs to be simple and convenient for the user to perform reliably, repeatedly, and safely.

A further problem is that the quantities and/or proportions of each active agent making up the combination therapy may need to be varied for each user or at different stages of their therapy. For example one or more active agents may require a titration period to gradually introduce a patient up to a "maintenance" dose. A further example would be if one active agent requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Another potential problem may stem from the fact that an increasing number of drug delivery devices, such as pen type drug delivery devices, are being marketed, including ones that are used for the delivery of different types of drugs. The issue of device and/or drug differentiation is becoming of increased importance as there can arise certain safety issues (some life-threatening) associated with a patient or user mistaking one drug delivery device for another device and then administering an incorrect or wrong drug. While device/drug differentiation can be achieved in a number of ways, a preferable method of differentiation is mechanical prevention (i.e., making it difficult or nearly impossible for a device/drug mix up to occur). As just one example, a number of commercially available pen type drug delivery devices are supplied with a dispense interface coupling mechanism that is non-proprietary. That is, with such a dispense interface, the coupling mechanism accommodates the attachment of a conventional Type A needle assembly via a helical thread. For such 'mono-product' devices, the use of different Type A needle assemblies is acceptable, as the needle assembly in this instance is simply the means of administering the medicament from the primary reservoir of the drug delivery device.

This may not be the case for Applicants' presently disclosed needle module and systems, where inadvertent use of a needle module with a non-approved primary delivery device could have serious consequences (e.g., such consequences could include unknown health risks as the two formulations may not have been subject to any clinical evaluation or perhaps lacks regulatory approval). Equally, the use of a standard Type A needle with the approved primary drug delivery device may not be desirable in a delivery device system comprising a medicated module, as a patient would not receive the targeted combination dose. In one situation, this might result in reduced therapeutic efficacy. However, in a worse situation, use of a standard Type A needle with the approved primary drug delivery device could result in non-desirable side effects (e.g., in the instance where the secondary medicament had some kind of balancing, cancelling or delaying effect on the pharmaco-kinetics ("PK") and/or pharmaco-dynamics ("PD") of the primary medicament contained within the drug delivery device). There are therefore certain safety and clinical benefits to configuring a combination delivery device so as to prevent attachment of a needle module to an incorrect primary drug delivery device. There are also, therefore, certain benefits (e.g., regarding safety and clinical benefits) to configure a combination delivery device so as to prevent attachment of a standard or conventional Type A needle to the combination therapy's primary drug delivery device.

Additional problems can arise where a multi-drug compound therapy is required, because many users cannot cope with having to use more than one drug delivery system or make the necessary accurate calculation of the required dose combination. This is especially true for users with dexterity or computational difficulties. In some circumstances it is also necessary to perform a priming procedure of the device and/or needle cannulae before dispensing the medicaments. Likewise, in some situations, it may be necessary to bypass one drug compound and to dispense only a single medicament from a separate reservoir.

Other problems can arise where a user is called upon to dispense a dose of medicament by way of a delivery device having a manually operated dose administration button. With such a button, the user is called upon to manually push or act upon the button to administer a dose while the dispense interface remains inserted at the injection site. This might cause problems for certain frail users or users with poor dexterity, especially those who might be required to hold down the dose injection button for a certain period of time (e.g., 10 seconds or so) to make sure that the selected dose has been properly administered. Other problems could also arise where the dispense interface is inserted into an injection site at an incorrect insertion depth and dose administration occurs at an incorrect depth.

SUMMARY

Accordingly, there exists a strong need to provide devices and methods for the delivery of one or more medicaments in a single automatic injection or delivery step that is simple for the user to perform and that can ensure a certain degree of dose accuracy at the proper injection depth. In one arrangement, the present system and methods include an automatic delivery device system that comprises a dose injecting mechanism comprising a triggering mechanism. An activating member, such as a needle guard of a needle module, can be used to initiate the triggering mechanism of the delivery device to thereby automatically enable the device to administer the set dose. Dose administration can occur without the user being called upon to provide a certain amount of force to activate a dose button. By using a secondary device such as the needle module to activate dose administration, the depth of needle penetration during dose administration can also be controlled so as to ensure proper medicament dispense when the dispense interface (e.g., a needle) is at a desired needle penetration depth. In one arrangement, the dose injecting mechanism comprises a dose setting mechanism that allows a user to select or set the administered dose. In an alternative arrangement, the single dispense interface may comprise a medicated module containing at least one dose of a secondary medicament.

In an alternative arrangement, the present system and methods can overcome the above-mentioned problems by providing separate storage containers for two or more active drug agents that are then only combined and/or delivered to the patient during a single delivery procedure. Administering a dose of one medicament automatically administers a fixed or determined dose of the second medicament (i.e., non-user settable). In one arrangement, the disclosed systems and methods also give the opportunity for varying the quantity of one or both medicaments. For example, one fluid quantity can be varied by changing the properties of the injection by varying or changing the device's "fixed" dose of the secondary drug package. As just one example, the second fluid quantity can be changed by manufacturing a variety of secondary drug containing packages with each variant containing a different volume and/or concentration of the second active agent. The user or healthcare professional would then select the most appropriate secondary package or series or combination of series of different packages for a particular treatment regime.

In one arrangement, a medicated module is provided that automatically causes the reservoir of a secondary medicament to come into fluid communication with the primary medicament upon activation of a needle guard. This eliminates the need for the user to manually set or adjust the medicated module after performing a priming step. \

These and other advantages will become evident from the following more detailed description of the invention.

One aspect of the present invention relates to a form of delivery device that does not comprise a separate user activated dose button or triggering mechanism so as to allow a user to manually trigger a preset dose. Rather, the delivery device is configured such that it can be used to administer a dose (settable or non-settable) only if the delivery device is attached to a secondary device. This secondary device may be configured to include an activating member that is allowed to initiate activation of the triggering mechanism after a certain dose administration step has taken place. For example, such a dose administration step could comprise the movement of a needle guard of a needle module during a dose administration step.

In another aspect, our invention allows complex combinations of multiple drug compounds within a single drug delivery system. The invention allows the user to use an automatic delivery device (e.g., a pen type auto-injector or an electro-mechanical type device) and dispense a multi-drug compound device through a single dispense interface attached to an automatic delivery device. This delivery device controls the mechanism of the device such that a predefined combination of the individual drug compound may be delivered when a single dose of one of the medicaments is set, a triggering mechanism is activated by a separate device, and then the predefined compound is dispensed through the single dispense interface.

By defining the therapeutic relationship between the individual drug compounds, the proposed delivery devices, systems and methods could help ensure that a patient/user receives the optimum therapeutic combination dose from a multi-drug compound device without the inherent risks associated with multiple inputs where the user has to calculate and set the correct dose combination every time they use the device. The medicaments can be fluids, defined herein as liquids or powders that are capable of flowing and that change shape at a steady rate when acted upon by a force tending to change its shape. Alternatively, one of the medicaments may be a solid that is carried, solubilized or otherwise dispensed with another fluid medicament.

Accordingly, one specific aspect of particular benefit to users with dexterity or computational difficulties is that the single input and associated predefined therapeutic profile removes the need for a user to calculate their prescribed dose every time they use the device and the single input allows considerably easier setting and dispensing of the combined compounds.

In one embodiment, a master or primary drug compound, such as insulin, contained within a automatic delivery device (e.g., a pen type automatic injector) could be used with a single use, user replaceable, needle module. The needle module may or may not contain at least one dose of a secondary medicament. The needle module further contains a single dispense interface (e.g., a needle module) and an activating member. When a triggering mechanism engages the activating member of the single dispense interface, a secondary compound contained within the needle module is administered on dispense of the primary compound.

According to the present invention the needle module may be attachable to the delivery device. The needle module may be detachable from the delivery device. The needle module may be releasably attachable to the delivery device. The needle module may comprise a connector configured for attachment to the delivery device. The connector may be configured for releasably connecting the needle module to the delivery device.

Although our invention specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with our invention.

For example, the purposes of our invention the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(w-carboxyheptadecanoyl)-des(B30) human insulin and B29-N-(ω-carboxyhepta¬ decanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH2).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

In one arrangement, Applicants' needle module comprises a needle guard. The needle module may also comprise a medicated module containing at least one dose of a secondary medicament. In one such needle guard arrangement, the module is attachable to the delivery device that comprises an outer housing having a proximal end, a distal end, and an outer surface, where the proximal end preferably has a hub holding a double-ended needle and having a connector configured for attachment to the delivery device. The module may also contain a reservoir in a bypass housing within the outer housing that contains a medicament. The module assembly may contain a needle guard that can reduce the risk of accidental needle sticks before and after use, reduce the anxiety of users suffering from needle phobia as well as preventing a user from using the device a subsequent time when the additional medicament has already been expelled.

The needle guard is preferably configured with a solid planar surface at its distal end that provides a large surface area that reduces the pressure exerted on the patient's skin, which allows the user to experience an apparent reduction in the force exerted against the skin. Preferably, the planar surface covers the entire distal end of the guard with the exception of a small needle pass through hole aligned axially with the needle. Preferably, the pass through hole size should be large enough for the user to see that the device is primed (i.e., a drop or more of medicament) while not being so large that it is still possible to reach the end of the needle with a finger (i.e. needle stick injuries before or after use). This difference between the hole size and cannula diameter is to allow for tolerances, to allow users to see the drop of liquid on the end of the cannula after priming (whether a transparent or non-transparent guard is used) while keeping the size small enough to prevent accidental needle stick injuries.

Further, the movable needle guard or shield is configured to move axially in both the distal and proximal directions when pressed against and removed from an injection site. When the needle assembly is pressed against the injection site, a proximal end of the needle guard acts as an activating member so to engage and then activate a triggering mechanism and thereby initiate a dose administration step of the delivery device. More preferably, when the needle assembly is pressed against the injection site, one or more needle guard prongs engage the triggering mechanism. In one most preferred arrangement, the system may be configured such that initiation of a dose administration step occurs at a specific injection depth, e.g., less than or equal to 12 mm. As just one example, in a specific example, the system is configured such that initiation of a dose administration step occurs at an injection depth about approximately 5-10 mm In one arrangement, when the needle assembly is removed or withdrawn from the patient, the guard is returned to post-use extended position. A drive tooth on the inside surface of the guard engages a stop on a track on the outer surface of the bypass housing to securely lock the guard from further substantial axial movement. Preferably a lock out boss on the outer surface of the bypass housing is configured to engage a lock out feature on the inner proximal surface of the outer housing at the completion of the injection to further lock the medicated module from any further use and prevent the needle(s) and/or bypass component from being able to substantially move within the system even if the guard is held in an axially locked condition. By "substantial" movement we do not mean the typical amount of "play" in a system, but instead we mean that the guard and/or distal needle do not move axially a distance that exposes the distal end of the cannula once it is locked out.

One goal of our invention is to eliminate the need to have the user manually operate a dose injection button on the drug delivery device to administer a dose. Another goal of our invention is to eliminate the need to have the user manually set a dose of the primary medicament contained within the drug delivery device. Another goal of the present invention is to eliminate the need for the user to manually operate the medicated module to change the state of the module from a priming state to a combination dose delivery state. Manually operated devices are sometimes not as intuitive as they could be and raise the risk of accidental misuse. One arrangement of Applicants' automatic delivery device solves this problem by utilizing energy stored within the delivery device to administer the dose automatically once the triggering mechanism has been activated.

One arrangement of Applicants' proposed medicated module utilizes energy stored within the module prior to delivery of the device to the user. The stored energy can come from a biasing member, such as a compressed spring. This stored energy is released during normal user operation of the module by actuating the mechanism and thus activating the state change from prime dose to combination dose. The mechanism aims to make this actuation imperceptible to the user, consequently making the user experience of the module very similar to that of a standard commercially available and accepted needle or safety needle (i.e., unpack module, attach to a auto-injector delivery device, prime auto-injector delivery device, administer a set dose along with single dose in the module). In this way, the module mechanism aims to reduce the risk of unintentional misuse and to improve usability by replicating an already accepted practice for similar injection methods.

The proposed needle module concepts can be designed for use with any automatic delivery device with an appropriate compatible interface. Such an automatic delivery device may be a single or multiple use delivery device. However, it may be preferable to design the needle module in such a way as to limit its use to one exclusive primary delivery device (or family of delivery devices) through employment of dedicated/coded/exclusive features to prevent attachment of a non-appropriate needle module to a non-matching delivery device. In some situations it may be beneficial to ensure that the module is exclusive to one particular type of delivery device while also permitting the attachment of a standard drug dispense interface to that same particular delivery device. This would allow the user to deliver a combined therapy when the module is attached, but would also allow delivery of the primary compound independently through a standard drug dispense interface in situations, such as, but not limited to, dose splitting or top-up of the primary compound.

A particular benefit of the presently disclosed delivery devices and systems is that the needle module makes it possible to tailor dose regimes when required, especially where a titration period is necessary for a particular drug. The needle module could be supplied in a number of titration levels with obvious differentiation features such as, but not limited to, aesthetic design of features or graphics, numbering etc, so that a patient could be instructed to use the supplied module in a specific order to facilitate titration. Alternatively, the prescribing physician may provide the patient with a number of "level one" titration medicated modules and then when these were finished, the physician could then prescribe the next level. A key advantage of this titration program is that the primary device remains constant throughout.

In a preferred embodiment, the primary delivery device is used more than once and therefore is multi-use; however, the delivery device may also be a single use disposable device, such as a disposable device. It is also possible to have a suite of different medicated modules for various conditions that could be prescribed as one-off extra medication to patients already using a standard drug delivery device. Should the patient attempt to reuse a previously used needle module, a presently disclosed embodiment includes a locking needle guard that is activated after a first predefined travel/retraction of the guard/insertion of the needle. The locked needle guard would alert the patient to this situation and the inability to use the module for a second time. Visual warnings (e.g. change in color and/or warning text/indicia within an indication window on the module once insertion and/or fluid flow has occurred) can also be used. Additionally, tactile feedback (presence or absence of tactile features on the outer surface of the module hub following use) could be used as well.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which.

DETAILED DESCRIPTION

The presently disclosed delivery device systems comprise a delivery device that does not require a user to manually activate a dose administration button. With such systems, a user can set a variable dose of a primary or first drug compound but the system or device can only administer this set dose if the device is properly triggered to administer the primary or first drug by a correct or dedicated secondary device (e.g., drug dispense interface or needle module). Such a secondary device comprises an activating mechanism for initiating the triggering mechanism. In such an arrangement, it is the activating mechanism of the drug dispense interface that enables the triggering mechanism of the primary delivery device to initiate dose administration. In one alternative arrangement, the presently disclosed delivery device systems comprise a delivery device that does not require a user to set a dose to be administered.

One advantage of such a system is that the delivery device cannot be dispensed without the secondary device properly attached. As such, this system could be used to prevent misuse of a delivery device intended to be used in combination or to implement exclusive operation means between families of delivery devices. As just one example, the present dose administration system prevents the primary medicament from being administered independently without use of a specialized or dedicated needle module, which may or may not contain a secondary medicament. Aside from the delivery systems herein illustrated, Applicants' proposed delivery systems could also be used in other fluid delivery systems such as specialized masks for gas lines, mouthpieces for inhalers or cannulae for intravenous or subcutaneous infusion, all of which would be prevented from dispensing a primary medicament unless the proper secondary device were attached to the primary delivery device.

Figure 1:
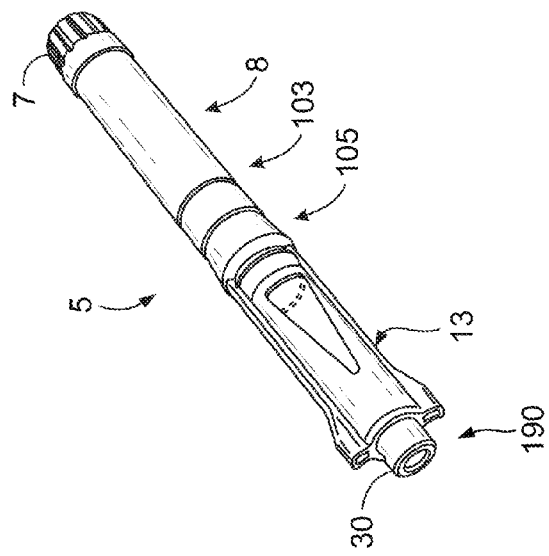
FIG. 1 illustrates a perspective view of one arrangement of an exemplary multi-use automatic delivery device that can be used with the present invention.

FIG. 1 illustrates a perspective view of one arrangement of an exemplary multi-use delivery device that can be used with the present invention. As can be seen from FIG. 1, unlike certain known pen type automatic delivery devices, Applicants' delivery device 5 does not comprise a manually activated trigger for allowing a user to manually initiate dose administration. Rather, and as will be explained in greater detail below, it is only after a dispense interface has been properly attached to a distal end of the device and it is only after an activation mechanism of this dispense interface has activated a triggering mechanism that the delivery device 5 automatically administer the set dose of the primary medicament contained within the delivery device.

Figure 2:
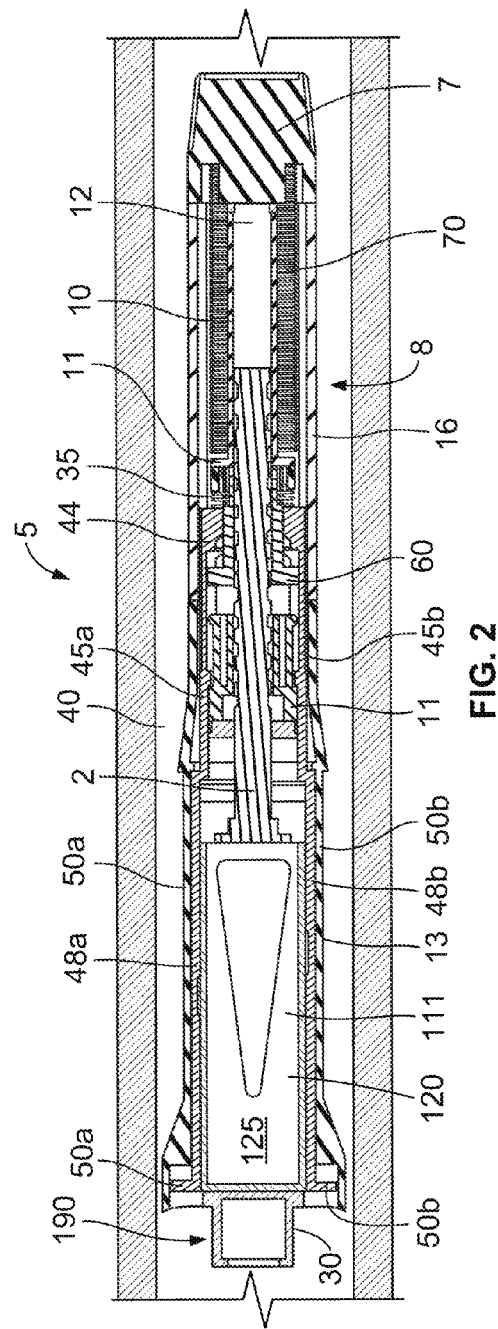
FIG. 2 illustrates a cross sectional view of the automatic delivery device illustrated in FIG. 1.

A schematic cross sectional view of the delivery device 5 illustrated in FIG. 1 is provided in FIG. 2. Referring now to FIGS. 1 and 2, the automatic delivery device 5 comprises two main assemblies: a dose injecting assembly or body 8 and a cartridge holder 13. The cartridge holder 13 may be used for holding a primary reservoir, such as an ampoule or cartridge containing a primary medicament, such as insulin. The dose injecting assembly 8 and cartridge holder assembly 13 of this automatic device are generally similar in design and operation to that described in U.S. Pat. No. 5,104,380 which is herein entirely incorporated by reference and to which the reader is directed to for further details. Such an automatic device may comprise a pen type auto-injector device provided by Owen Mumford Limited of Oxford, England under the tradename of AutoPen. However, one major difference between the automatic devices illustrated and described in U.S. Pat. No. 5,104,380 and Applicants' proposed delivery device as illustrated in FIGS. 1-2 is that Applicants' proposed delivery device does not utilize a manually activated triggering mechanism for initiating dose administration. Rather, in one arrangement of Applicants' proposed drug delivery devices and systems, the member for activating a dose administration step is provided by a separate secondary device, such as by way of a needle guard on a needle module or a medicated module. Although the automatic delivery device is illustrated as a pen type delivery device, Applicants' system and method of dose administration can use other forms of delivery devices where the driving force used to dispense the primary medicament contained within the device is not provided by the user at the time of dose dispense or administration.

The automatic drug delivery device 5 illustrated in FIG. 1 is just one type of automatic delivery device that can be used with Applicants' needle module 140 (see FIGS. 6-11 and 13-20). This needle module 140 could be releasably attached to a connection means 190 provided near a distal end 30 of the cartridge holder 13. Applicants' needle module 140 is preferably self-contained and may be provided as a sealed and sterile disposable module that has an attachment means compatible to the attachment means 190 at the distal end 30 of device 5. As will be described in greater detail below, in one arrangement, Applicants' needle module 140 may comprise a medicated module wherein this medicated module comprises a reservoir containing a secondary medicament.

Although not shown, the needle module 140 could be supplied by a manufacturer in a protective and sterile container, where the user would peel or rip open a seal or the container itself to gain access to the sterile needle module. In some instances it might be desirable to provide two or more seals for each end of the medicated module.

Figure 21:
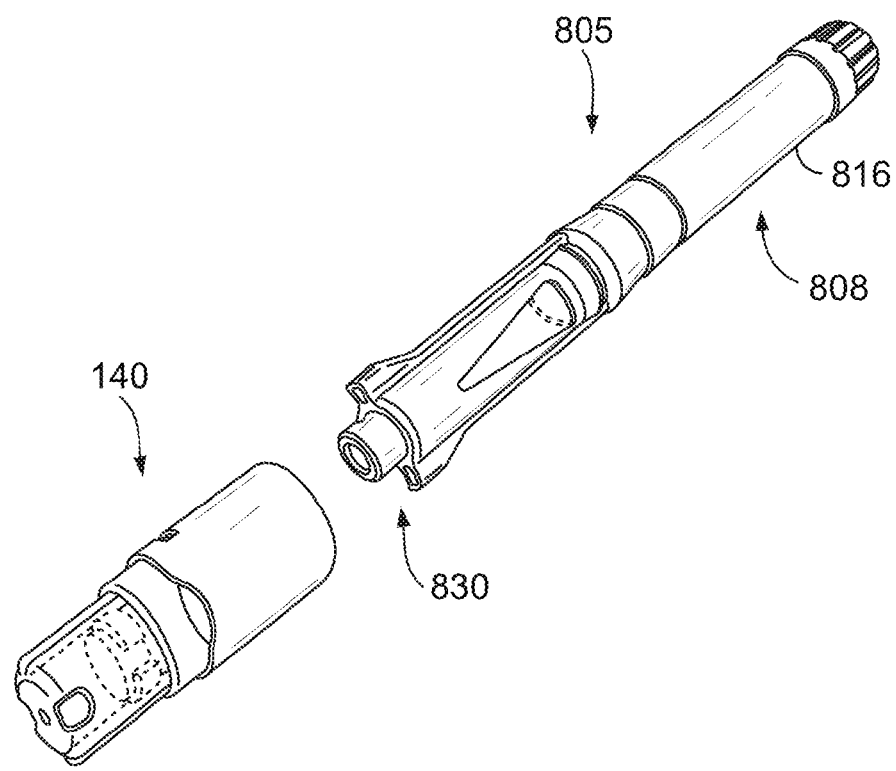
FIG. 21 illustrates a perspective view of one arrangement of an exemplary single-use automatic delivery device that can be used with the present invention.

The delivery device 5 is in the form of a multi-use pen type automatic delivery device. A proximal end 105 of the cartridge holder 13 and a distal end 103 of the dose injecting mechanism 8 are removably secured together. The delivery device may comprise a re-usable or a disposable delivery device. Where the device comprises a reusable device, the cartridge holder 13 and the dose injecting mechanism 8 are removably secured to one another. In a disposable or single use delivery device, the cartridge holder 13 and the dose injecting mechanism 8 are permanently secured to one another. As just one example of such a disposable device, FIG. 21 illustrates one arrangement of a single-use automatic delivery device that can be used with the proposed delivery systems and methods disclosed herein.

As will be explained in greater detail below, to inject a previously set dose, a properly dedicated dispense interface (e.g., a double ended needle module or needle assembly) is attached to the coupling mechanism 190 provided near the distal end 30 of the cartridge holder 13. For example, in one preferred arrangement, the coupling mechanism 190 provided near the distal end 30 of the cartridge holder 13 may comprise a standard thread (or other suitable connecting mechanism such as a snap lock, snap fit, form fit, or bayonet lock mechanism) so that the drug dispense interface may be removably attached to the distal end of the cartridge holder 13.

Figure 5:
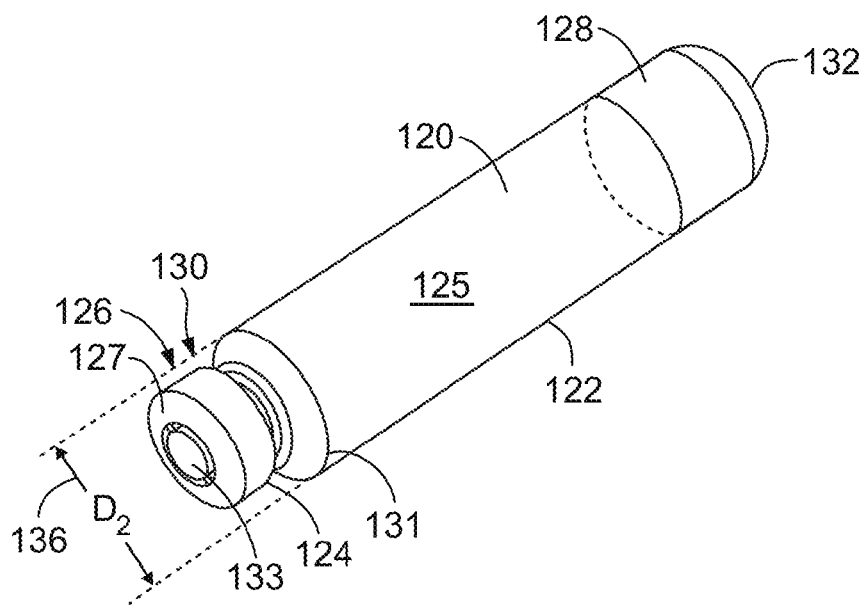
FIG. 5 illustrates one arrangement of a cartridge or ampoule that may be used with the delivery device illustrated in FIGS. 1-3.

The cartridge holder 13 defines an inner cartridge cavity 111 and this inner cavity 111 is dimensioned and configured to securely receive and retain the ampoule or cartridge 120. FIG. 5 illustrates a perspective view of a cartridge 120 that may be used with the delivery device 5 illustrated in FIGS. 1-3. The cartridge 120 includes a generally tubular barrel 122 extending from a distal end 130 to a proximal end 132. The distal end 130 is defined by an inwardly converging shoulder 131.

At the distal end 130, the cartridge 120 includes a smaller diameter neck 126 and this neck projects distally from the shoulder 131 of the barrel 122. Preferably, this smaller diameter neck 126 is provided with a large diameter annular bead 133 and this bead extends circumferentially thereabout at the extreme distal end of the neck 126. A pierceable seal or septum 127 is securely mounted across the open distal end defined by the neck. The seal 127 may be held in place by a metallic sleeve or ferrule 124. This ferrule 124 may be crimped around the circumferential bead at the distal end of the neck. The medicament 125 is pre-filled into the cartridge 120 and is retained within the cartridge, in part, by the pierceable seal 127, the metallic sleeve 124, and the stopper 128. The stopper 128 is in sliding fluid-tight engagement with the inner tubular wall of the barrel 122. Axially directed forces acting upon the stopper 128 during a dose injection step or dose administration step urges the medication 125 from the cartridge though a double ended needle mounted onto the distal end 30 of the cartridge holder 13 and then into an injection site. For example, if the cartridge 120 is provided in the cartridge holder 13 of delivery device 5, such axial forces may be provided by the piston rod 2 of the dose injecting mechanism 8 of device 5.

A portion of the cartridge holder 104 defining the cartridge holder cavity 111 is of substantially uniform diameter. This diameter D1 134 is preferably slightly greater than the diameter D2 136 of the cartridge 120. The interior of the cartridge holder 13 includes an inwardly-extending annular portion or stop that is dimensioned to prevent the cartridge 120 from moving within the cartridge holder 13. In this manner, when the cartridge 120 is loaded into the cavity 111 of the cartridge holder 13 and the cartridge holder 13 is then connected to the dose injecting member 8, the cartridge 120 will be securely held within the cartridge cavity. More particularly, the neck 126 and ferrule 124 of the cartridge 20 are inserted in a proximal to distal direction into the open proximal end of the cartridge holder 13 with the ferrule eventually passing entirely into the holder 13. With the holder 13 secured to the dose injecting mechanism 8, the proximal end of the cartridge 120 will typically abut a stop provided by the dose setting member 8.

In one arrangement, where the cartridge comprises more than one dose, a number of doses of a primary medicament 125 may be dispensed from the cartridge 120. It will be understood that the cartridge 120 may contain a type of medicament that must be administered often, such as one or more times a day. One such medicament is insulin. A movable piston 128 (FIG. 5) is retained in a first end or proximal end of the cartridge 120 and receives an axial force created by the piston rod 2 of the dose injecting mechanism 8.

In an alternative cartridge arrangement, the cartridge 120 may comprise only a single dose of a primary medicament. In such an arrangement, where the delivery device comprises a reusable device, once the single dose has been administered, the cartridge holder would have to be released from the dose injecting mechanism so that the empty cartridge could be replaced with a fresh cartridge. In such an arrangement where the delivery device comprises a single use device such as the device 800 illustrated in FIG. 21, once the single dose has been administered, the device would be discarded.

Now referring to the illustrations provided in FIGS. 1-4, the various component parts of the automatic delivery device 5 and their interactions with one another will be described. As illustrated, the dose injecting mechanism 8 comprises a body 16. This body may be used to house a dose dial grip 7, a triggering mechanism 40, a trigger spring 35, a drive gear 60, a trigger spring 35, a drive shaft 10, and a reset dial 11. The dose injecting mechanism 8 further comprises a piston rod 2, such as a threaded piston rod that advances in a distal direction (i.e., towards the injection site) when a previously set dose is to be injected or administered.

The triggering mechanism 40 may comprise a multi-component triggering mechanism. In this illustrated arrangement, the triggering mechanism 40 may comprise two component parts: a trigger 44 and two elongated trigger fingers 48 *a,b*. In this illustrated arrangement, the elongated trigger fingers 48 *a,b* extend from the distal end 30 of the cartridge holder 13 towards the dose injecting mechanism 8 so as to mechanically link the distal end of the cartridge holder 13 with the dose injecting mechanism 8. The proximal end of the trigger fingers 48 *a,b* are configured to be removably secured to the trigger 44. Specifically, the trigger fingers 48 *a,b* comprise first and second trigger finger arms 50 *a,b*. These trigger finger arms 50 *a,b* are configured to releasably cooperate with an activation member (such as a needle guard of a needle module) so that the dose setting member can be activated to administer or dispense a previously set dose.

There are certain advantages of utilizing a two part triggering mechanism in a reusable delivery device. For example, because of the two part structure of the triggering mechanism 40, the cartridge holder 13 may be released from the dose injecting mechanism 8 so as to replace a spent cartridge. That is, when the cartridge holder 13 is released from the dose injecting mechanism 8, the elongated trigger fingers 48 *a,b* remain with the cartridge holder 13 while the trigger 44 remains with the dose injecting mechanism 8. When the cartridge holder 13 is re-connected to the dose injecting mechanism 8, the trigger fingers 48 *a,b* will re-engage the trigger 44.

Alternatively, where the delivery device 5 comprises a disposable or a single use delivery device, this triggering mechanism 40 could comprise a unitary component since in such a configuration the cartridge holder 13 would not need to be releasably coupled from the dose injecting mechanism 8.

Figure 3:
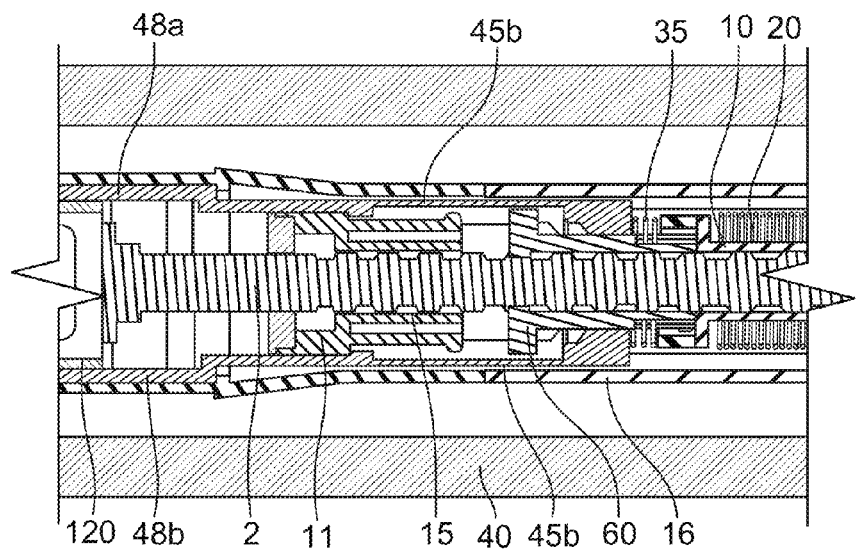
FIG. 3 illustrates a close up view of a portion of the cross sectional view of the delivery device illustrated in FIG. 2.
Figure 4:
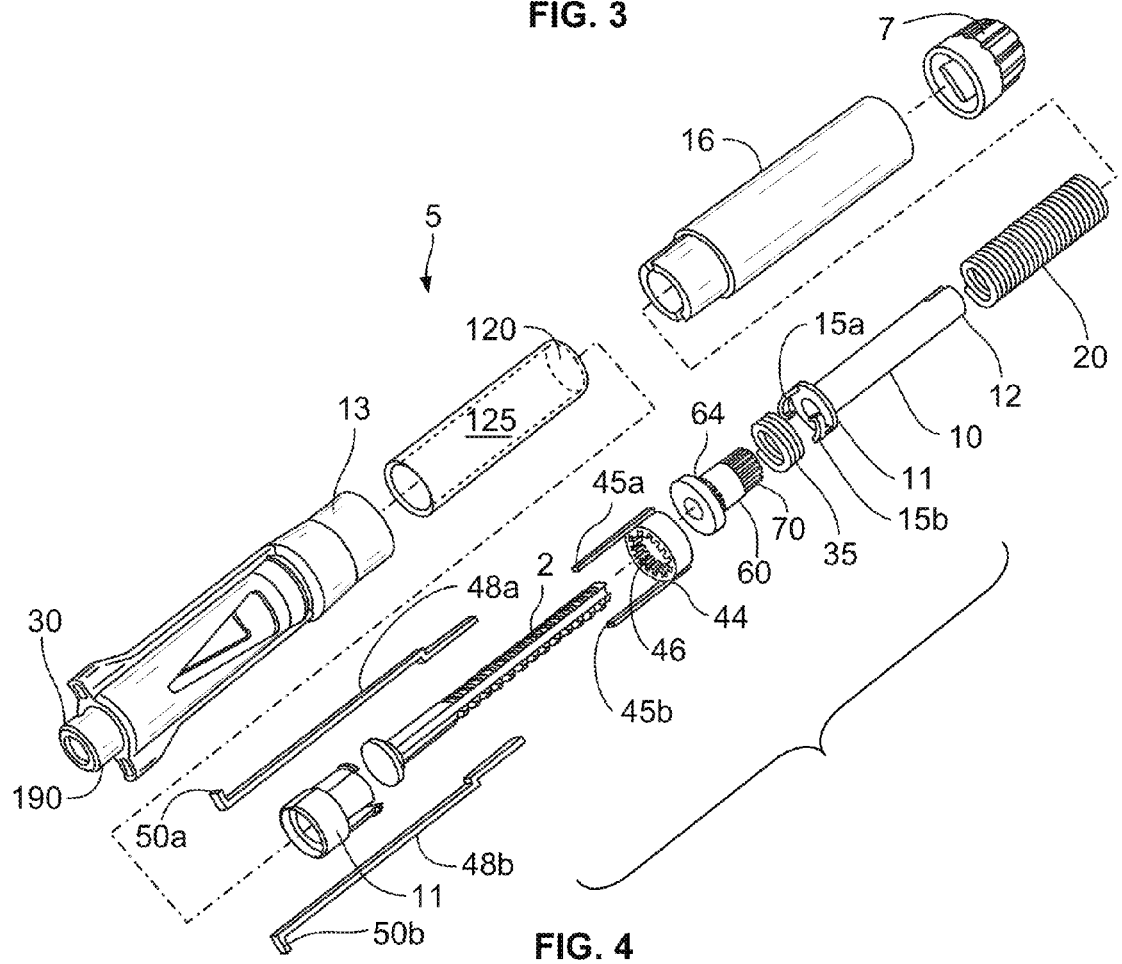
FIG. 4 illustrates an exploded view of the various component parts making up the exemplary delivery device illustrated in FIG. 1.

The triggering mechanism 40 further comprises a trigger 44. The trigger 44 is shown in a most distal position shown in FIGS. 2 and 3. This trigger 44 comprises two trigger arms 45 a,b that extend towards the distal end 30 of the cartridge holder 13. These two arms 45 a,b are configured to be releasably coupled to a respective elongated fingers 50 a,b of the trigger fingers 48. As illustrated in FIG. 4, the trigger 44 also comprises an inner radial surface that comprises a plurality of teeth 46. These trigger teeth 46 engage a plurality of corresponding teeth 64 provided on a flange of the drive gear 60.

The dose injecting mechanism 8 of the delivery device 5 further comprises two biasing members: a primary biasing member 20 and a secondary biasing element 35. Preferably, the primary member 20 comprises a torsion spring and the secondary member comprises a compression spring. As illustrated in FIGS. 2 and 3, the secondary member 35 is positioned between a proximal end of the trigger 44 and a distal end of the drive sleeve 10. In this position, this secondary element exerts pressure in the distal direction on the proximal face of the trigger 44 so that the plurality of teeth 46 of the trigger 44 mesh with the plurality of teeth 64 of the drive gear 60. As such, as long as these two sets of teeth 46, 64 mesh under the force exerted by the secondary biasing member 35, the trigger 44 will prevent the drive gear 60 from rotating and hence, through its threaded engagement with the piston rod 2, from driving the piston rod 2 in a distal direction.

The secondary biasing member 35 acts between a distal end 11 of the drive shaft 10 and the proximal end of the trigger 44 to bias both the trigger 44 and the drive gear 60 together. This second biasing member 35 acts so as to urge the trigger 44 in the distal direction. Urging the trigger 44 in the distal directions acts to maintain the trigger's 44 engagement with the drive gear 60. For example, the trigger spring 35 acts to bias the internal teeth 46 of the trigger 44 to mesh with the flange teeth 64 provided by the drive gear 60. If these two sets of teeth were not biased together, the gear 60 would be allowed to rotate and through its threaded engagement with the piston rod 2, drive the piston rod in a distal direction.

The dose injecting mechanism 8 further comprise a dose dial grip 7. This grip 7 is provided near a proximal end of the dose injecting mechanism 8 and is operably coupled to one end of the primary biasing element 20 and rotationally coupled to the drive shaft 10. The other end of the primary biasing element 20 is fixed to the body 16 or a retainer component (not shown) that is itself keyed against rotation within the body 16. When a user sets a dose by turning the dose dial grip 7, the primary biasing member 20 is wound up against its engagement with body 16. Since the drive gear 60 is rotationally coupled to dose dial grip 7, this also rotates. However, the drive shaft 10 is coupled to the drive gear 60 through a unidirectional coupling, such as a ratchet afforded by the ratchet arms 15a and 15b acting on splined teeth 70 of drive shaft 10. As such, when the dose dial grip 7 is released by the user, these ratchet teeth prevent the drive shaft 10 from back-winding without the coupled rotation of drive gear 60. However, as discussed above, the trigger 44 acts to prevent the drive gear 60 from rotating and hence from allowing the delivery device 5 to administer the set dose.

The piston rod 2 is formed with an integral quick pitch screw thread cooperating with a corresponding internal thread in the bore of the drive gear 60. As such, rotation of the drive gear 60 will cause axial movement of the piston rod 2 in the distal direction. Rotation of the drive gear 60 continues until an external projection on the dose dial grip 7 comes against a stop consisting of an internal projection formed on device housing 16 when the preset dose will have been discharged from the cartridge by the piston rod 2.

The piston rod 2 is prevented from rotation during dose dispense. Preferably, the piston rod 2 is prevented from rotating during dose dispense by two opposed axial flats formed on the piston rod 2 and locating in a correspondingly shaped hole in the reset dial 11. This reset dial can also act as a rewind knob on a reusable device.

The dose injecting mechanism 8 is closed at its distal end by a reset dial 11. This reset dial 11 may be screwed into the dose injecting mechanism 8. Preferably, the body 16 comprises a cylindrical boss extending in the distal direction and is externally threaded so as to accommodate the cartridge holder 13. The cartridge or ampoule 20 of a primary medicament 125, such as either a short acting or a long acting insulin, is provided into the cartridge holder 13. Where the device 5 comprises a reusable device, after the cartridge 20 has been placed within the cartridge holder 13, the cartridge holder may be releasably connected onto a boss on the body 16.

The reset dial 11 guides longitudinal movement of the piston rod 2 either during a dose administration step or during a resetting step. The reset dial 11 guides the piston rod 2 progressively into the open end of the cartridge 120 as the primary medicament 125 is injected through a dose dispense interface coupled to the distal most end 30 of the cartridge holder 13. In one arrangement, the reset dial 11 comprises a bore. Preferably, this bore has opposed flats for preventing rotation of the piston rod 2 as the piston rod 2 moves into the cartridge 20 during a dose administration step.

Importantly, in the delivery device 5 illustrated in FIGS. 1-3, movement of the piston rod 2 in the distal direction may be achieved, in part, by energy stored in a primary biasing member 20. As a user sets a dose of the primary medicament 125 to be injected by turning the dose dial grip 7, the primary biasing member 20 becomes twisted under tension. Therefore, a dose of the primary medicament 125 to be administered is set by rotation of a dose dial grip 7 which cannot turn about a drive shaft 10 at the proximal end of the dosing mechanism 8. The dose dial grip 7 may be provided with a pointer, marker or window featuring graduations that can be read to show the angle through which the cap has been turned relative to body 16 and thereby provide a reading of the dose being dialed.

The dose of the primary medicament 125 contained within the cartridge 120 may be set by turning the dose dial grip 7 about body 16. The dose dial grip 7 is fastened to other components of the dose injecting mechanism 8 such as the drive shaft 10, one end of the primary biasing member 20 and is coupled to body 16 such that relative rotation is permitted but relative axial movement is not. The other end of the biasing member 20 may be locked to body 16. As such, any rotation of dose dial grip 7 relative to housing 16 will build up a torque in biasing member 20 as one end of it is rotated by dose dial grip 7 and the other end is held rigidly in body 16.

During a dose setting step, when the dose dial grip 7 is rotated, the user can count the clicks as the ratchet tooth moves over successive teeth on the gear 60. In addition, the user can also observe the movement of a scale provided on the dose dial grip 7 in relation to a pointer, marker or window that may be provided along an outer surface of the body 16. This enables the user to set the preset dose visually as well as aurally.

After a dose has been set with the delivery device as described above, without a proper needle module attached to the delivery device, this set dose will not be administered since the delivery device 5 does not comprise a manually activated dose button. Rather, an activating member for initiation dose administration is provided by way of a secondary device, such as a needle module (such as the needle module 140 illustrated in FIG. 6) coupled to the delivery device 5. This module can be used to activate the triggering mechanism 40 so as to release the drive gear 60 and thereby allow the drive gear 60 to rotate. Then, under the torque exerted by the primary biasing member 20, through their threaded engagement the freely rotatable drive gear 60 drives the piston rod 2 in a distal direction to thereby allow the delivery device 5 to administer a set dose.

Figure 6:
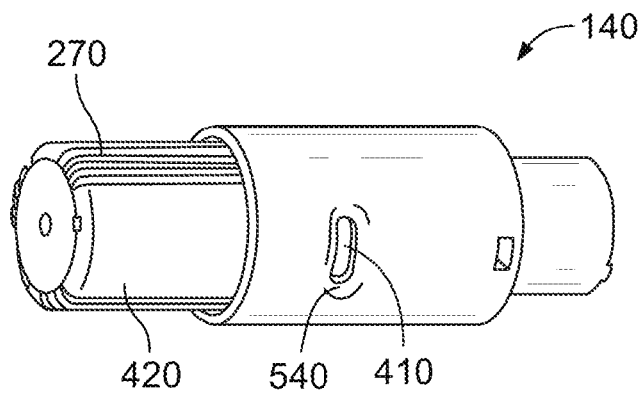
FIG. 6 illustrates an embodiment of a needle module of the present invention, where the needle module is separated from a primary reservoir of a delivery device, such as the primary reservoir of the delivery device illustrated in FIG. 1.

After the dose has been set, the delivery device must be activated to administer the dose. Activation occurs by moving the trigger mechanism 40 in the proximal direction so that the trigger 44 disengages from the drive gear 60 and allows the drive gear 60 to rotate. One way to activate this trigger mechanism 44 is by attaching a needle module to the delivery device and utilizing a needle guard of this module to activate the triggering mechanism. One such needle module that may be used with Applicants' automatic delivery device is illustrated in FIG. 6. For example, FIG. 6 illustrates an embodiment of a needle module 140 for use with Applicants' delivery device 5, where the needle module 140 is separated from a primary reservoir of a delivery device, such as the primary reservoir of the delivery device illustrated in FIG. 1.

As previously described, the delivery device 5 comprises a coupling mechanism 190 for releasably coupling a needle module, such as the medicated module 140 illustrated in FIG. 6. As just one example, in one arrangement, the delivery device 5 may include a coupling mechanism 190 in the form of a threaded section 121. This threaded section 121 of the delivery device 5 threadably couples a corresponding attachment means or connector 180 on the delivery device 140. (See, e.g., FIG. 5). Alternatively, in another delivery device arrangement, other known coupling mechanisms 190 can be used to attach the needle module to the distal end of the drug delivery device. This could include types of permanent and/or removable connection means, such as threads, snap locks, snap fits, luer locks, bayonet, snap rings, keyed slots, and combinations of such connections.

In some situations, however, it may be also beneficial to ensure that the needle module 140 is exclusive to only one type of or one family of delivery devices. One advantage of such an arrangement is that such a situation would allow the user to deliver a combined therapy only when the needle module 140 is attached to the drug delivery device. In such a situation, the needle module could have an exclusive interface such that it can only be used with one such dedicated delivery device for reasons such as safety.

For example, in one delivery device system, a range of medicated modules could contain a variety of medicaments for various situations/scenarios all of which could be delivered in combination with the medicament from the delivery device (primary device). It is also possible that the delivery device contains only a buffer solution or dilutant to dispense a concentrated medicament from the medicated module.

Figure 7:
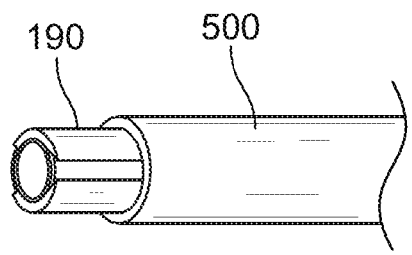
FIG. 7 illustrates an embodiment of a dedicated coupling mechanism that can be used to attach a needle module to the distal end of a drug delivery device, such as the delivery device illustrated in FIGS. 1-3.
Figure 14:
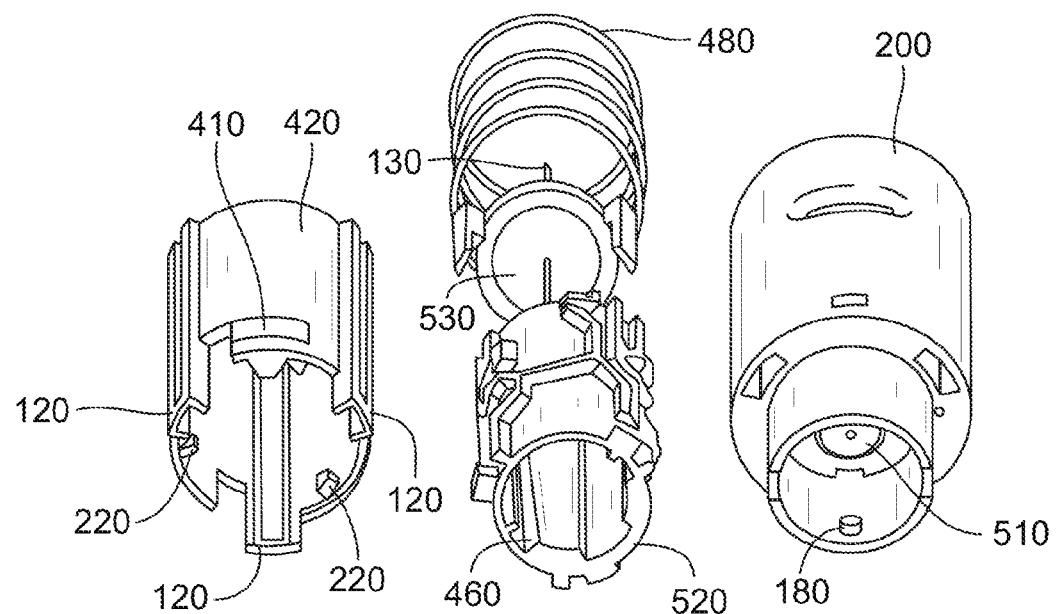
FIG. 14 illustrates an exploded proximal perspective view of all the components (except the medicated capsule) of the needle module illustrated in FIG. 6.

For example, FIGS. 7 and 14 illustrate one type of dedicated coupling means 190 of a drug delivery device, such as the delivery device 5 illustrated in FIGS. 1-3. As illustrated, this attachment means 190 comprises a unique bayonet type connection that is keyed specifically to a corresponding female bayonet type connection 180 on hub 510 of medicated module 140 (See FIG. 14).

Figure 8:
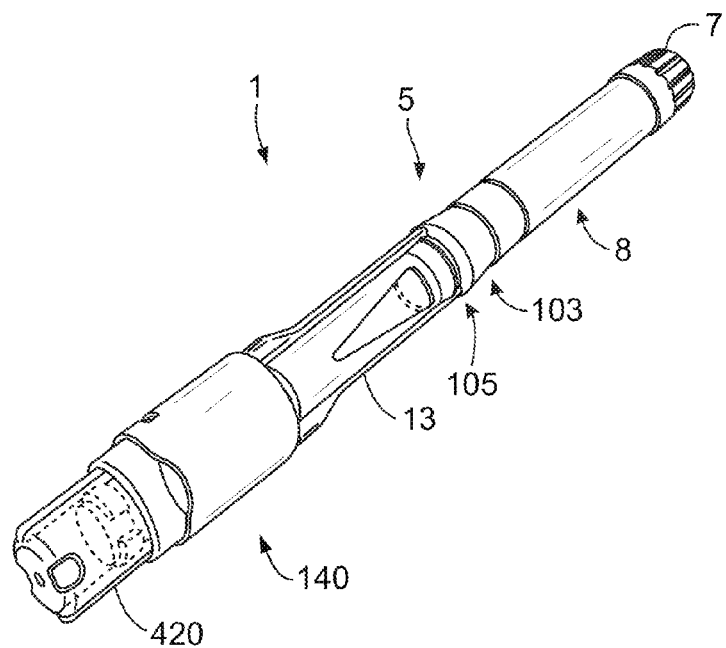
FIG. 8 illustrates a needle module attached to a primary reservoir of a delivery device, such as the primary reservoir of the delivery device illustrated in FIGS. 1-3.
Figure 9:
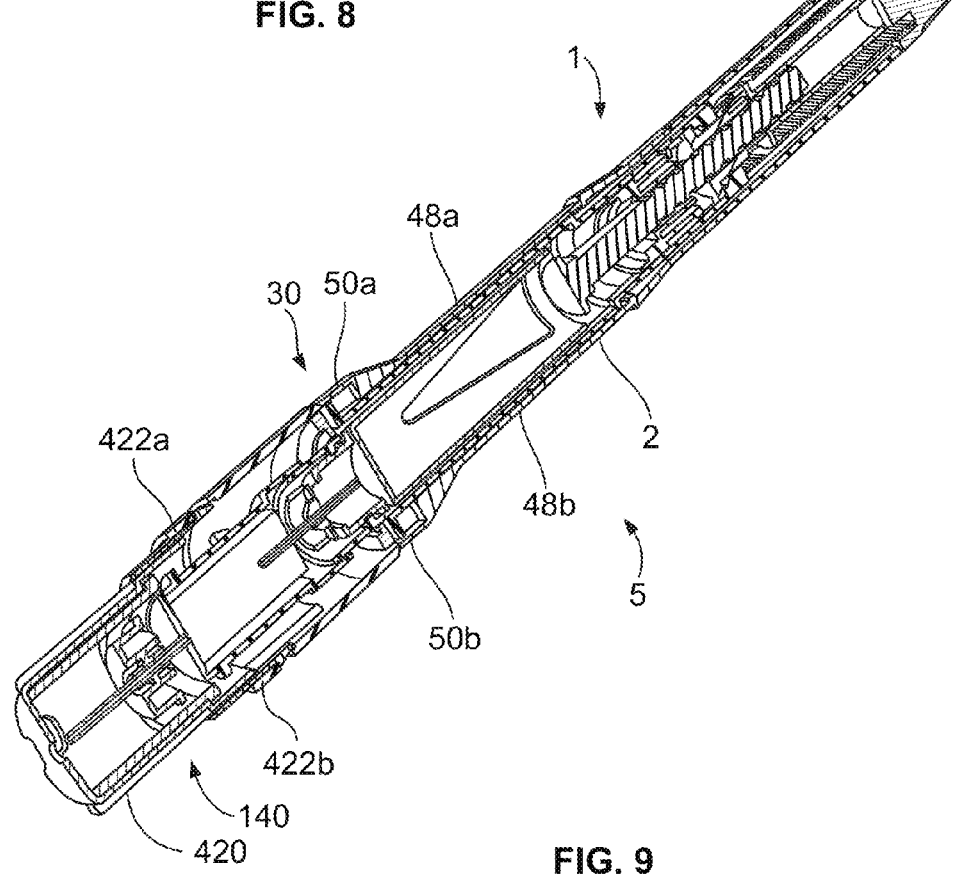
FIG. 9 illustrates a cross section view of the needle module attached to a distal end of the delivery device as illustrated in FIG. 8 of the needle module attached to a distal end of the delivery device.
Figure 10:
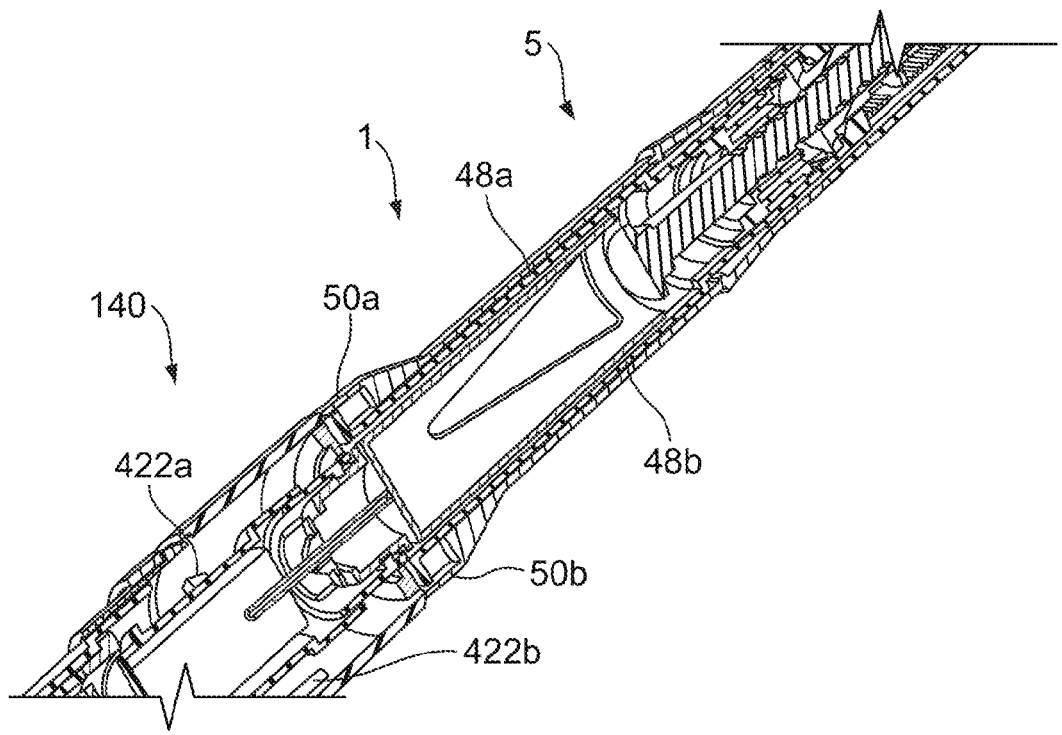
FIG. 10 illustrates a close up view of the cross sectional view illustrated in FIG. 9 of the needle module attached to a distal end of the delivery device.

FIG. 8 illustrates a delivery system comprising the needle module illustrated in FIG. 6 releasably attached to the delivery device 5 illustrated in FIGS. 1-3. In this illustration, a proximal needle contained within the needle module resides in fluid communication with the primary reservoir contained within the delivery device 5. This may be seen more clearly from FIG. 9. FIG. 9 illustrates a cross section view of the needle module 140 attached to a distal end 30 of the delivery device as illustrated in FIG. 8 of the needle module attached to a distal end of the delivery device;

FIG. 10 illustrates a close up view of the cross sectional view illustrated in FIG. 9 of the needle module attached to a distal end of the delivery device of the drug delivery system 1. As illustrated, prongs 422 a,b near the proximal end of the needle guard 420 have not yet initiated contact with the arms 50 a,b of the trigger fingers 48 a,b, respectively, of the triggering mechanism 40.

Figure 11:
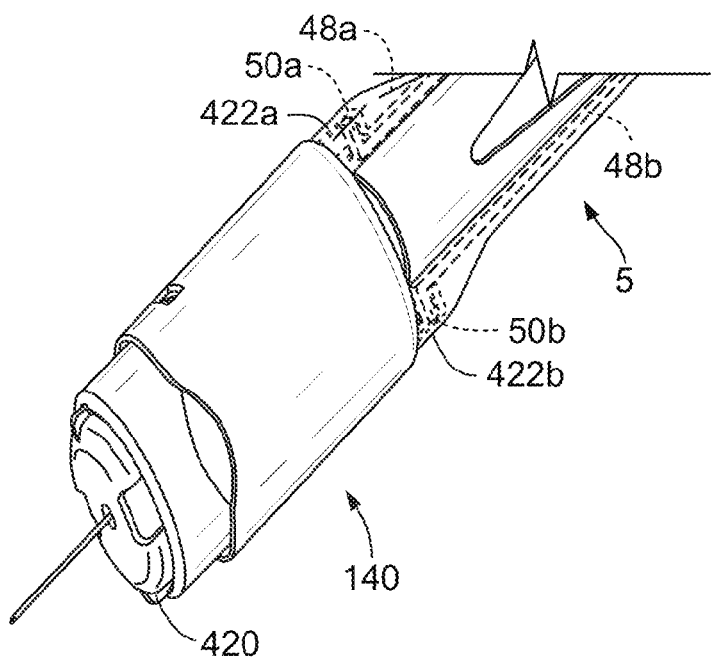
FIG. 11 illustrates a close up view of the needle module attached to a delivery device during a dose administration step where the activating element of the needle module begins to engage a distal end of the triggering mechanism of the delivery device.

To administer a dose with this delivery device system 1, the user presses the needle module 140 against an injection site. When the distal end of the needle guard 420 engages the injection site, the needle guard 420 is driven back against the primary device 5. For example, FIG. 11 illustrates a close up view of the needle module 140 attached to a delivery device 5 during a dose administration step where the actuation element of the needle module (i.e., the needle guard 420) begins to move in the proximal direction and to initiate contact with a distal end of the actuation triggering mechanism 40 of the delivery device. And FIG. 12 illustrates a close up view of the delivery device 5 illustrated in FIG. 9 during a dose administration step where the actuation element of the needle module 420 begins to engage a distal end of the actuation triggering mechanism of the delivery device.

Figure 12:
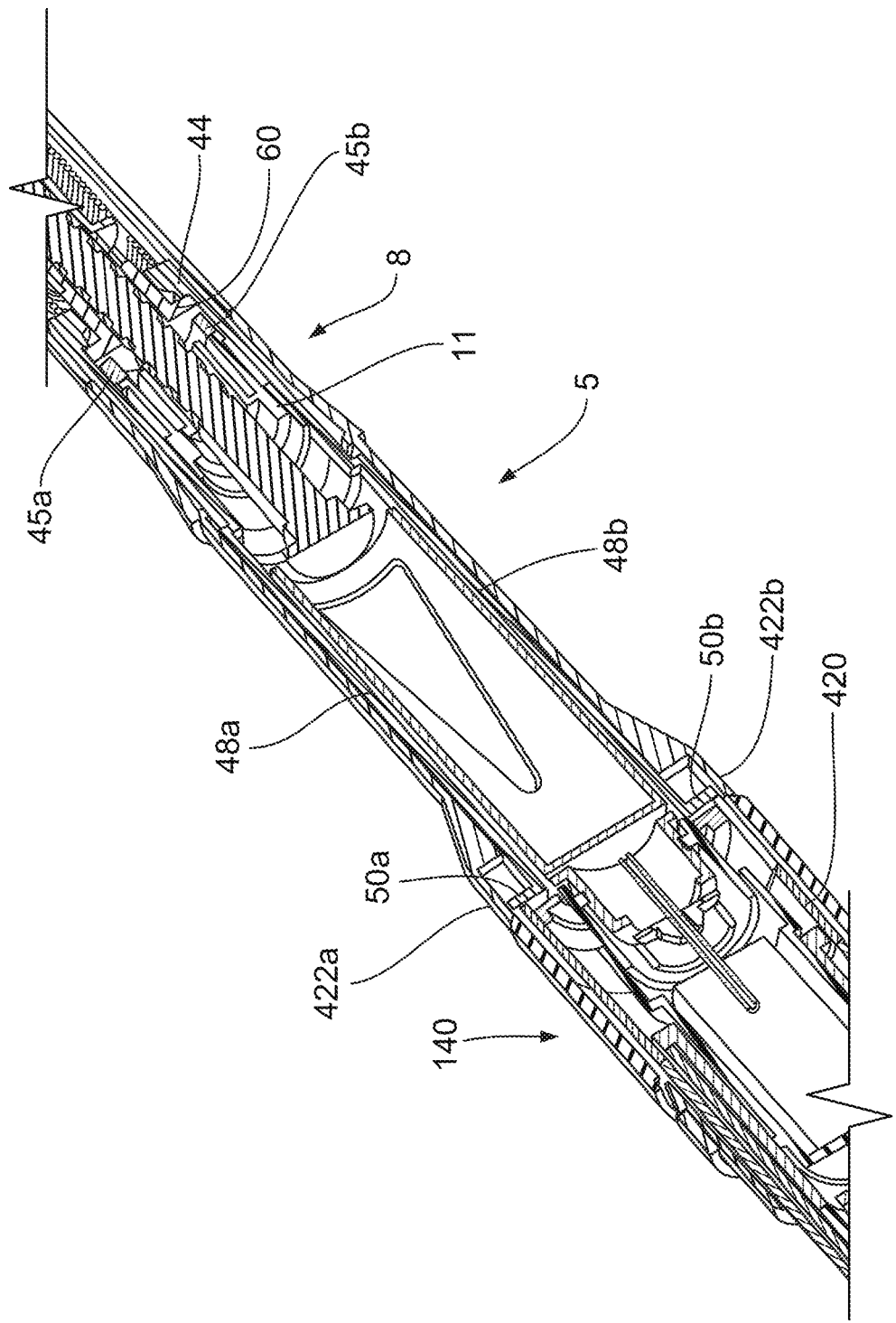
FIG. 12 illustrates a close up view of the delivery device illustrated in FIG. 9 during a dose administration step where the activating element of the needle module begins to engage a distal end of the triggering mechanism of the delivery device.

Referring now to FIGS. 11 and 12, as the needle guard 420 begins to move in the proximal direction, the needle guard 420 proximal end contacts the distal end of the trigger mechanism 40 and begins to move the elongated trigger fingers 50 a,b. Preferably, the needle guard 420 proximal end comprises first and second prongs 422 a,b and these prongs contact the elongated trigger fingers arms 50 a,b such that these trigger fingers 48 a,b are pushed back in the proximal direction. For example, FIGS. 11 and 12 illustrate the needle guard prongs 42 a,b of the needle guard 420 initiating contact with the arms 50,b of the trigger fingers 48 a,b.

As contact between the needle guard prongs 422 a,b and the trigger finger arms 50 a,b is initiated, the trigger fingers 48 a,b are pushed back in the proximal direction towards the dose injecting mechanism 8. This may be seen from FIG. 12 which illustrates a close up view of the delivery device 5 illustrated in FIG. 9 during a dose administration step where the activating element of the needle module begins to engage a distal end of the triggering mechanism 40 of the delivery device 5.

As the trigger fingers 48 a,b move in a proximal direction, because these fingers 48 a,b are mechanically coupled to the trigger arms 50 a,b of trigger 44, the mechanically coupled trigger 44 is pushed in the proximal direction against the action of the second biasing member 35. Trigger 44 moves proximally, overcoming second biasing member 35, until the plurality of trigger teeth 46 are moved out of engagement with the corresponding teeth 64 of the drive gear 60. For example, as can be seen from FIG. 12, the trigger 44 has been moved out of engagement with the drive gear 60. As such, the drive gear 60 is now free to rotate. As the drive gear 60 is now free to rotate, this allows the drive shaft 10 to rotate with it in the opposite direction to that required to dial a dose, due to the ratcheted engagement between the components. As the dose dial grip 7 and one end of the energized biasing member 20 are also connected to the drive shaft 10, the release of drive gear 60 allows the energy stored in primary biasing member 20 to be released. As such, the first biasing element 20 can now unwind and thereby rotate the dose dial sleeve 7, drive shaft 10 and the drive gear 60.

Rotation of the drive shaft 10 and hence the drive gear 60 act to drive the piston 2 distally due to the threaded engagement between drive gear 60 and piston rod 2. The piston rod is therefore driven forward dispensing the primary medicament 125 through the secondary device 140. Where the secondary device 140 comprises a medicated module containing at least one dose of a secondary medicament, as the piston rod is driven forward, it will dispense any secondary medicament contained in the needle module as well as the set dose of the primary medicament 125 through the secondary device.

To set a subsequent dose of the primary medicament 125 contained with cartridge 20, the needle module 140 is removed from the injection site. This allows the trigger arms 50 a,b and trigger fingers 45 a,b to extend in the distal direction as second biasing element 35 is allowed to relax. The relaxation of second biasing element 35 also pushes trigger 44 in the distal direction and engages it with drive gear 60, preventing any further dispensing of primary medicament as the next dose is dialed. The dose dial grip 7 is then turned through the desired number of stops. Then, when a proper replacement needle module 140 is attached to the delivery device 5 and an activating member of the needle module activates the triggering mechanism, a further dose may be ejected.

Multiple injections may continue until the cartridge is exhausted. Where the auto-injector 5 comprises a reusable auto-injector, the cartridge holder 13 may be removed from the dose setting mechanism 8 by unscrewing the housing connector 43. Removing the dose setting mechanism 8 from the holder 13 releases the reset dial 11 for rotation in relation to the dose setting mechanism 8. As such, the reset dial 11 can now act as a rewind knob. That is, the reset dial 11 can be turned by hand or piston rod 2 can be pushed axially and overhauled against its threaded engagement to drive gear 60 to drive the piston rod 2 back in the proximal direction to an initial piston rod starting position. This will allow the user to insert a fresh cartridge into the cartridge holder 13. Then, when the housing connector 43 is re-engaged, the reset dial is locked in position ready for further operation.

Figure 22:
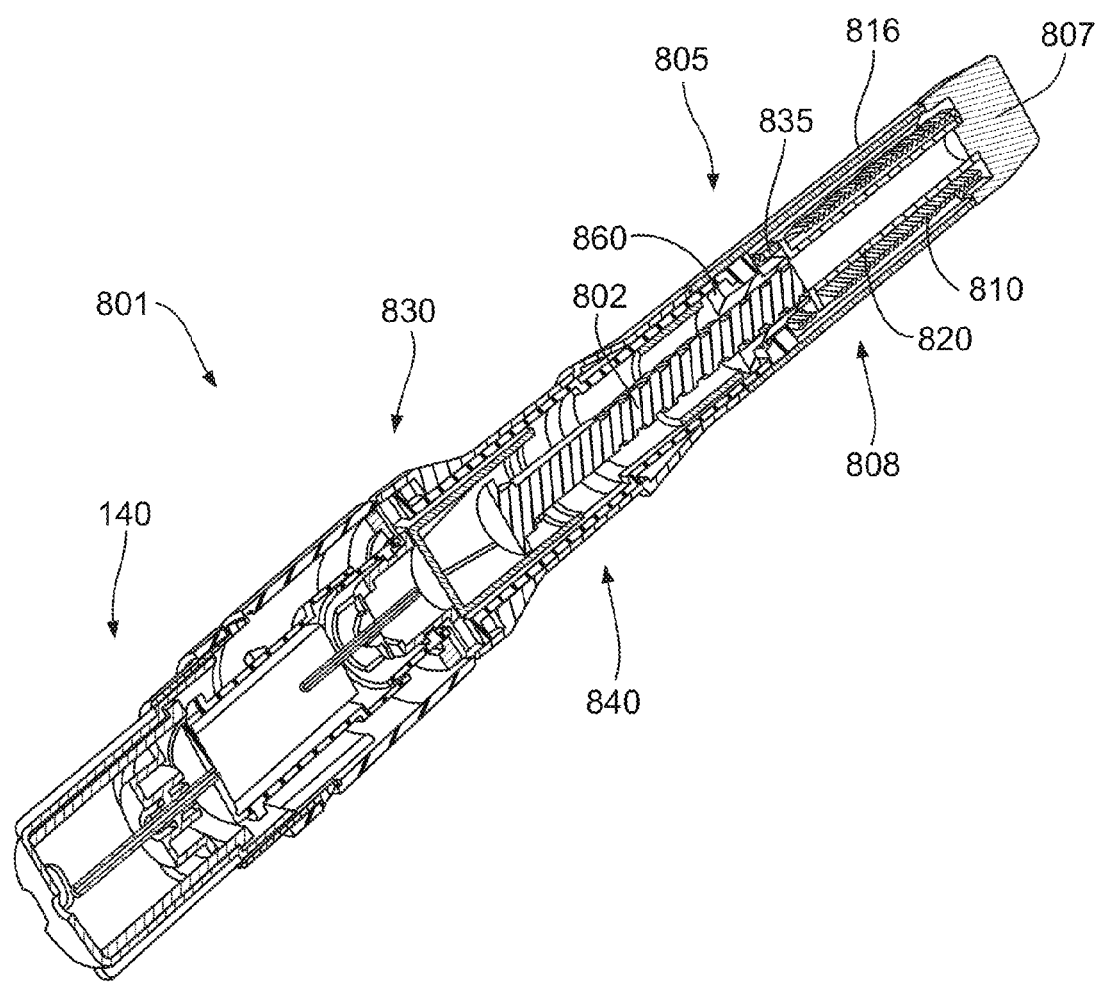
FIG. 22 illustrates a cross section view of a needle module attached to a distal end of the delivery device as illustrated in FIG. 8 of the needle module attached to a distal end of the delivery device illustrated in FIG. 21.

Alternatively, where the device 5 comprises a single use delivery device, the user merely disposes of the device and retrieves a prefilled auto-injector for subsequent injections. For example, FIG. 21 illustrates a perspective view of one arrangement of an exemplary single-use automatic delivery device that can be used with the present invention, such as the needle module 140. FIG. 22 illustrates a cross section view of the needle module 140 attached to a distal end 830 of the delivery device 805 illustrated in FIG. 8.

Figures 19, 20:
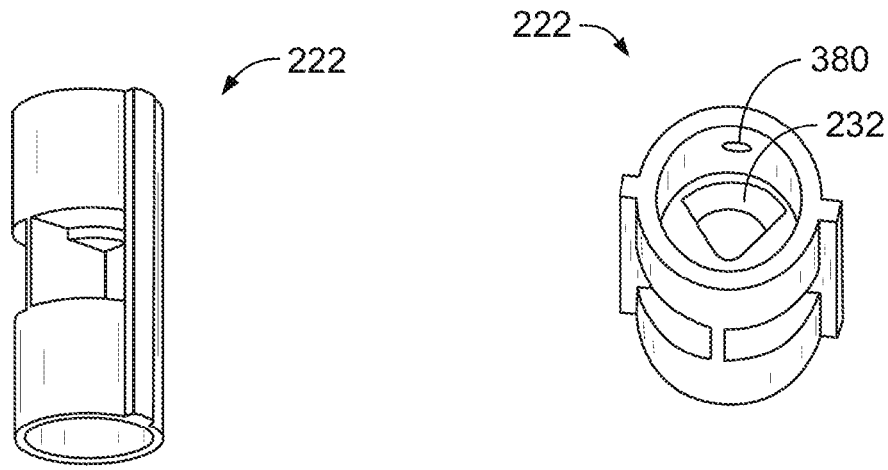
FIG. 19 illustrates one possible embodiment of a reservoir for use with the needle module illustrated in FIG. 6.
FIG. 20 illustrates one possible embodiment of a flow distributor for use with the needle module illustrated in FIG. 6.

As may be seen from FIGS. 21 and 22, the single use device 805 has a similar mechanical structure as delivery device 5. For example, as illustrated, single use device 805 comprises a dose injecting mechanism 808 comprises a body 816. This body may be used to house a triggering mechanism 840, a trigger spring 835, a drive gear 860, a trigger spring 835, a primary biasing element 820, and a drive shaft 810. The dose injecting mechanism 808 further comprises a piston rod 802, such as a threaded piston rod that advances in a distal direction (i.e., towards the injection site) when a previously set dose is to be injected or administered. One difference, however between the dose injecting mechanism 8 of FIG. 1-3 and the dose injecting mechanism 808 illustrated in FIGS. 20 and 21 is that dose injecting mechanism 8 allows a user to set a dose via dose dial grip 7. In contrast, the dose injecting mechanism 808 has no dose dial grip since the device 805 is provided to the user already set. This is accomplished by providing the primary biasing element 820 in a pre-wound state before the end cap 807 is fitted to the body 816 of the dose injecting mechanism 808.

Another difference may that the triggering mechanism 840 of delivery device 805 may comprise a unitary component. For example, as previously mentioned, where the delivery device 805 comprises a disposable or a single use delivery device, this triggering mechanism 840 could comprise a unitary component since in such a configuration the cartridge holder 813 would not need to be releasably coupled from the dose injecting mechanism 808.

Administering a dose of with Applicants' delivery device system 801 is similar to the system 1 previously described. For example, similar to the multi-use device 5, without a proper needle module attached to the singe use delivery device 805, this pre-set dose will not be administered since the delivery device 805 does not comprise a manually activated dose button. Rather, an activating member for initiation dose administration is provided by way of a secondary device, such as a needle module (such as the needle module 140 illustrated in FIG. 6) coupled to the delivery device 805, can be used to activate the triggering mechanism 840 so as to release the drive gear 860 and thereby allow so the drive gear 860 to rotate. Then, under the pre-wound force exerted by the primary biasing member 820, the freely rotatable drive gear 860 drives the piston rod 802 in a distal direction to thereby now allow the deliver device 805 to administer a set dose.

One advantage of Applicants' proposed drug delivery system is that, since the user does not need to manually hold down a dose dispense button during the dose administration step, compliance with certain injections that require a certain amount of dispense time (e.g., some injections are suggested as 10-second dispense times) is more likely. In addition, such a delivery system also tends to reduce the possibility for partial or incomplete dosing (i.e., releasing a user activated dose dispensing button too early) may also prove more intuitive.

Another advantage of such a delivery system is that because the dose is delivered by an internal automatic drive mechanism (such as the primary biasing element or a motor) and not by a drive mechanism that requires user force, there is no longer a requirement for a user to hold down a button for a length of time, while the device is inserted, to ensure dose accuracy. This may be of particular use to frail users or those with poor dexterity.

Another advantage of the delivery device system is that the activating member of the needle module 140 can be configured to drive the trigger mechanism 840 in the primary device at a certain point during the dose administration step. The point of dispense can therefore be tailored to the depth of needle insertion if required. For example, the point at which the needle guard engages the distal end of the trigger mechanism during dose administration step can be tailored by varying the length of the needle.

Another advantage of such a system 1 is that the timing of the actuation of the primary device can be linked to the position of the secondary device relative to the user's skin. One advantage of this is that the drug is only dispensed when the needle is at the correct depth. In addition, with Applicants' system, there is no longer a requirement for the user to activate a discrete dispense button. This may improve device ergonomics as the dispense action is now combined with the needle insertion action. With this set-up, the user actions are now one step less than what is considered as current method administering: attach needle, dial dose, insert needle to injection site, dispense medicament, remove needle and discard. Now, with Applicants' proposed system, the act of dispensing the set dose now occurs as part of the insertion process.

FIGS. 6 and 13-20 illustrate one embodiment of a needle module comprising a needle guard. For example, FIGS. 7 and 14 illustrate an alternative attachment means 190 of a drug delivery device, such as the delivery device 5 illustrated in FIGS. 1-3 or the delivery device 805 illustrated in FIGS. 20 and 21. As illustrated, this attachment means 190 comprises a unique bayonet type connection that is keyed specifically to a corresponding female bayonet type connection 180 on hub 510 of medicated module 140. These illustrated embodiments have the benefit of the second medicament as a single dose being contained entirely within capsule 310, and specifically in reservoir 222, hence minimizing the risk of material incompatibility between the second medicament and the materials used in the construction of the medicated module 140, specifically housing 200, inner housing 520, or any of the other parts used in the construction of the medicated module.

Figure 15:
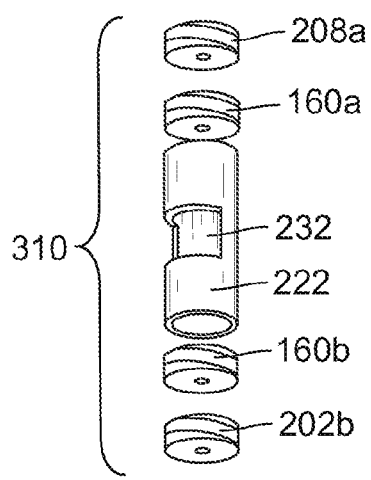
FIG. 15 is a perspective view of the capsule containing the reservoir of the embodiment of FIG. 6.
Figure 16:
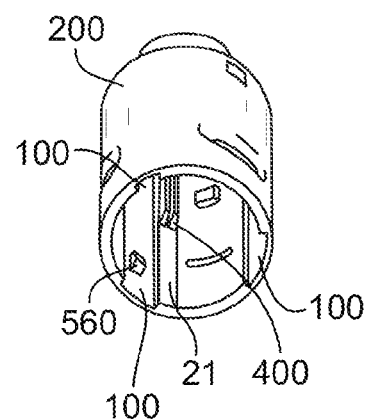
FIG. 16 illustrates a proximal perspective view of the outer housing of the needle module embodiment of FIG. 6.

To minimize the residual volume of the second medicament, caused by recirculation and/or stagnant zones, that might remain in capsule 310 at the end of the dispense operation, it is preferable to have a flow distributor 232 as an integral part of reservoir 222 (see FIGS. 15 and 19). The reservoir 222 containing the single dose of the secondary medicament can be sealed with septa 160a and 160b, which are fixed to the capsule using keepers or plugs 202a and 202b. Preferably the keepers have fluid channels that are in fluid communication with needles 130 and 150 and with bypass 460, which is preferably part of the inside surface of bypass housing 520. Together this fluid path allows priming of the drug delivery device before injection. Preferably the reservoir, flow distributor, keepers, and bypass can be made from materials that are compatible with the primary medicament. Examples of compatible materials of construction include, but are not limited to, COC (an amorphous polymer based on ethylene and norbonene, also referred to as cyclic olefin copolymer, ethylene copolymer, cyclic olefin polymer, or ethylene-norbornene copolymer); LCP (a liquid crystal polymer having an aramid chemical structure that includes linearly substituted aromatic rings linked by amide groups, and further can include partially crystalline aromatic polyesters based on p-hydroxybenzoic acid and related monomers and also highly aromatic polyesters); PBT (polybutylene terephthalate thermoplastic crystalline polymer or polyester); COP (a cyclic olefin polymer based on ring-opening polymerization of norbornene or norbornene-derivatives); HDPE (high density polyethylene); and SMMA (styrene methyl methacrylate copolymer based on methyl methacrylate and styrene). The needle pierceable septa, bungs, and/or seals that are used with both the capsule and the primary medicament cartridge can be manufactured using TPE (thermo plastic elastomer); LSR (liquid silicone rubber); LDPE (low density polyethylene); and/or any kind of medical grade rubber, natural or synthetic.

The design of flow distributor 232 should ensure that at least about 80% of the second medicament is expelled from reservoir 222 through the distal end of needle 130. Most preferably at least about 90% should be expelled. Ideally, displacement of the first medicament of a primary reservoir contained within a primary device, such as the multi-use delivery device 5 or single use device 805, and through the capsule 310 will displace the single dose of the second medicament stored in reservoir 222 without substantial mixing of the two medicaments.

Attachment of the medicated module 140 to the Applicants' delivery device causes proximal needle 150 to penetrate a septum sealing the distal end of the cartridge, and hence the primary reservoir 70 containing the primary medicament of the delivery device. For example, FIG. 9 illustrates the medicated module 140 attached to the device 5 where a proximal needle of the medicated module 140 pierces a septum of the cartridge contained within the delivery device 5 so that the proximal needle reside in fluid communication with the primary medicament 60 contained within the primary reservoir 70 of the auto-injector 5. Similarly, FIG. 22 illustrates the needle module 140 attached to device 805.

Once needle 150 of the medicated module 140 has passed through the septum 22 of the primary reservoir 70, fluid connection is made between the first or primary medicament 60 and the needle 150. At this point, the system can be primed by setting a small dose and then triggering the dosing mechanism 10 so that the piston rod 2 moves in the distal direction. As the piston rod 2 acts on the stopper contained within the cartridge, a small number of units of the first medicament 60 contained in the primary reservoir 70 will be expelled from the medicated module.

Once the device 5 is primed, then activation of the needle guard 420 allows dispense of the medicaments by subcutaneously injecting the medicaments via activation of the device 5 as previously described.

Figure 13:
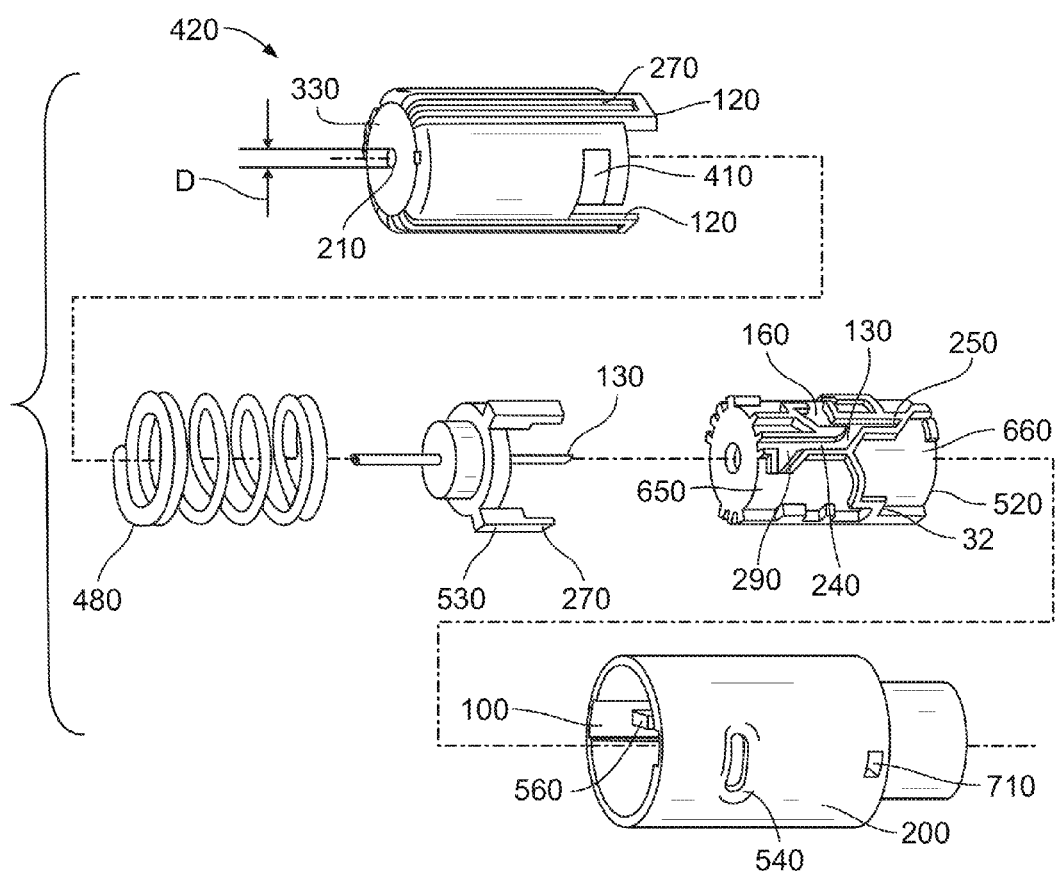
FIG. 13 illustrates an exploded distal perspective view of all the components (except the medicated capsule) of the needle module illustrated in FIG. 6.

One embodiment of the needle module 140 of our invention is illustrated in FIGS. 6 and 13. Where this needle module 140 comprises a reservoir of a secondary medicament, the needle module 140 comprises a medicated module.

In these embodiments the medicated module 140 contains a capsule 310 comprising a reservoir 222, two keepers 202a and 202b, and two seals 160a and 160b. Reservoir 222 contains a fixed single dose of a secondary medicament. In some cases this secondary medicament may be a mixture of two or more drug agents that can be the same or different from the primary drug compound in the drug delivery device 5. Preferably the capsule is permanently fixed within the medicated module, however, in some cases it may be preferred to design the module such that the capsule can be removed when empty and replaced with a new capsule.

Figure 17:
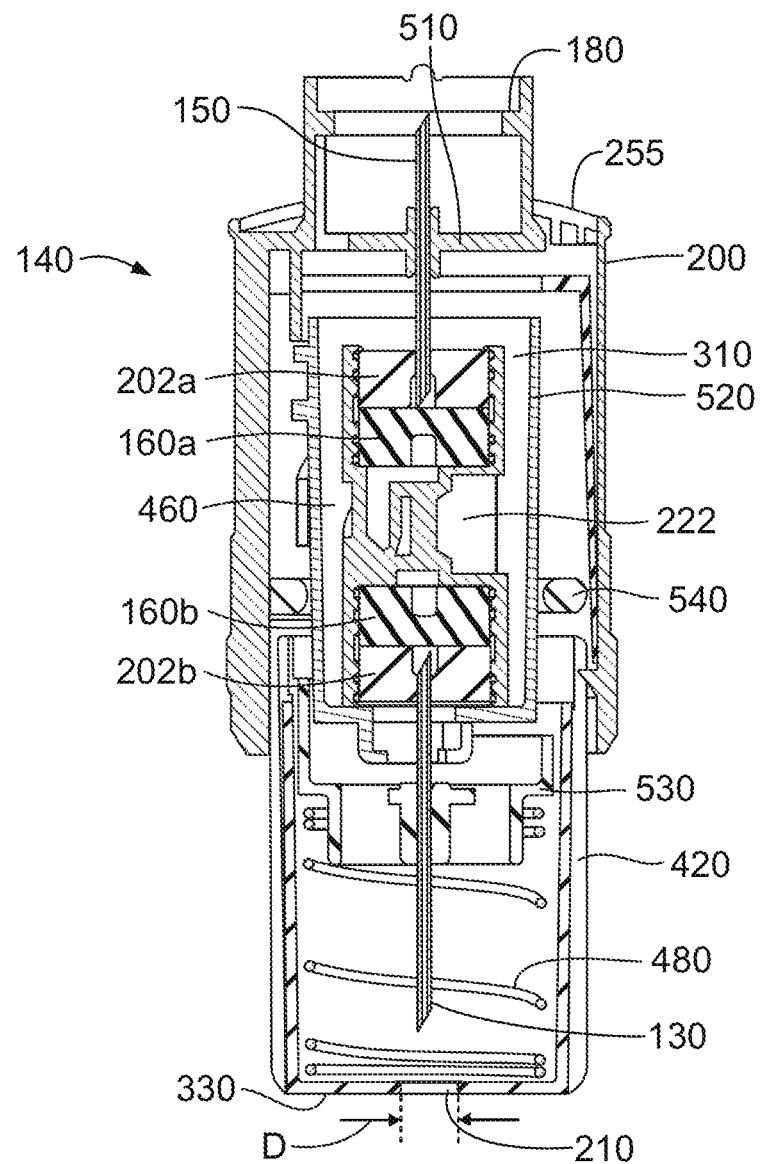
FIG. 17 is a sectioned view of the embodiment of the needle module shown in FIG. 6 orientated in the bypass configuration.

In the embodiments shown in FIGS. 15 and 17, capsule 310 has ends that are sealed with pierceable membranes or septa 160a and 160b that provide a hermetically sealed and sterile reservoir 222 for the second medicament. A primary or proximal engagement needle 150 can be fixed in hub 510 connected to the proximal end of housing 200 of the module and configured to engage capsule 310 when needle guard is moving in the proximal direction during injection. The outlet, or distal needle 130, is preferably mounted in lower hub 530 and initially protrudes into lower keeper 202b. The proximal end of needle 130 pierces the lower septum 160b when the bypass housing 520 rotates and is moved proximally by the force exerted by needle guard 420 and spring 480 during injection.

When first attached to the delivery device, the medicated module 140 is set at a pre-use or starting position. Preferably, indicator 410 shows through window 540 to inform the user of the pre-use condition of the medicated module. The indicator is preferably a color stripe or band on the outer surface of the proximal end of guard 420 visible through an aperture in the outer body. The needle guard 420 is slidably engaged with inner surface of outer housing 200 by engagement of arms 120 and channels 100. Retention snaps 560 prevent the guard from disengaging the outer housing at its fully extended position. Housing 200 partially defines an internal cavity 21 that holds bypass housing 520, which contains capsule 310. A portion of the proximal end of housing 200 defines an upper hub 510 that holds needle 150. Optionally, as illustrated in FIG. 17, a shoulder cap 255 may be added to the proximal outer surface of outer housing 200. This shoulder cap can be configured to serve as indicia to identify to a user the type/strength of medicament contained in the module. The indicia can be tactile, textual, color, taste or smell.

FIG. 17 shows a cutaway or cross-sectioned view of the medicated module set in a pre-use or starting state where needles 130 and 150 are not piercing septa 160a and 160b. In this position, the bypass housing 520 is at its most extended position and needles 130 and 150 are not in fluid communication with medicament contained in capsule 310. The capsule is supported by bypass housing 520. In this neutral or suspended state of capsule 310, primary medicament 60 from the primary reservoir 70 in the cartridge holder 13 of autoinjector 5 can flow through needle 150 into keeper 202a, through bypass 460 and into keeper 202b, and eventually out through needle 130. This flow configuration allows a user to perform a priming step or procedure by administering a small dose of the primary medicament using the dosing mechanism 10 the drug delivery device 5 without wastage of the primary medicament.

The compression spring 480 is positioned between the distal end of bypass housing 520 and the inner proximal face of guard 420 to bias the guard 420 into an extended (guarded) position as illustrated in FIG. 17. Upon assembly, spring 480 is purposely compressed to supply a proximally directed biasing force against lower hub 530. This pre-compression of spring 480 is possible because the lower hub 530 and the bypass housing 520 are prevented from moving in an axial proximal direction by radial stand off 400 located on the inside surface of the outer housing that engage with an upper stand off pocket 660 and legs 270 of lower hub 530 engaging lower stand off pocket 650. The combination of these standoffs/legs and pockets prevent the lower hub and upper hub needles from piercing into the centre of the capsule until the device is triggered as previously described.

The proximal inside surface of guard 420 has one or more inwardly protruding features, drive teeth, pips, or like structures 220 that run in one or more tracks 230 or guide ways formed in the outer surface of bypass housing 520. As shown in FIG. 13, track 230 can be described as four paths, 290, 240, 250, and 260, that have a specific geometry such that after a single use of the medicated module 4 the drive tooth 220 is blocked from further axial movement and the guard (and device) is "locked" in a guarded position where the distal end of the needle is completely and safely covered by guard 420.

One unique feature of our medicated module assembly is the user feedback that is given when the assembly is used. In particular, the assembly could emit an audible and/or tactile "click" to indicate to the user that they have firstly triggered the device and secondly reached the "commit" point such that the needle guard will lock safely out upon completion of the injection/removal of the guard from the injection site. This audible and/or tactile feature could work as follows. As mentioned, the needle guard 420 is rotationally constrained by outer housing 200 and has one or more drive teeth 220 that are initially in path 290 of track 230 on bypass housing 520. As the guard is moved proximally, the spring 480 is further compressed exerting additional force in the proximal direction on lower hub 530, which is initially constrained axially by the lower stand off pocket 650 engaged with legs 270. Likewise, the bypass housing 520 is constrained from moving proximally by upper stand off pocket stop 732 engaged with stand off 400 on the inner surface of outer housing 200. The drive teeth 220 travel in path 290 causing the bypass housing to rotate slightly. This rotation will disengage the upper stand off 400 from upper standoff pocket stop 832, allows the drive teeth to enter path 240, and unblocks legs 270 from lower standoff pocket allowing the bypass housing to move proximally carrying with it capsule 310, where it then can engage needles 130 and 150. As the guard continues to move proximally, the drive teeth move from path 240 passed transition point 240a into path 250 causing further rotation of the bypass housing. As this rotation is completed the drive teeth transition to path 230, potentially emitting an audile "click" sound, as well as a tactile feel, to the user. This transition past point 250a (and the corresponding point directly below it on the track) constitute the "commit" point and as such, once it has been reached the needle guard 420 will "lock out" when it extends upon removal of the device from the injection site.

As mentioned, the distal end of the guard 420 has a planar surface 330 that provides an added measure of safety and reduces the pressure exerted by the guard on the injection site during an injection with our needle assembly. Because the planar surface 330 substantially covers access to needle 130 a user is prevented from gaining access to the distal tip of the needle after the assembly is in the locked position. Preferably, the diameter D of needle pass through hole 210 in the planar surface is no more than 10 times that of the outer diameter of needle cannula 130.

The outer proximal surface of the needle guard 420 preferably has indicia 410 that are preferably at least two different color stripes or bands, each of which is sequentially visible through the opening or window 540 in outer housing 200. One color could designate the pre-use or prime state of the module and the other color would indicate that the module is in finished or locked state, another color could be used to denote the transition through the trigger or "commit" point in case a user stops injection after trigger point but before "commit" point. For example, a green color could be the pre-use position and a band of red color could be used to indicate that the module has been used and is locked and an orange color could indicate that the device has been triggered but not locked out. Alternatively, graphics, symbols or text could be used in place of color to provide this visual information/feedback. Alternatively these colors could be displayed using the rotation of the bypass cavity and printed on or embedded into the bypass housing. They could be visible through the aperture by ensuring that the needle guard is made form a transparent material.

Figure 18:
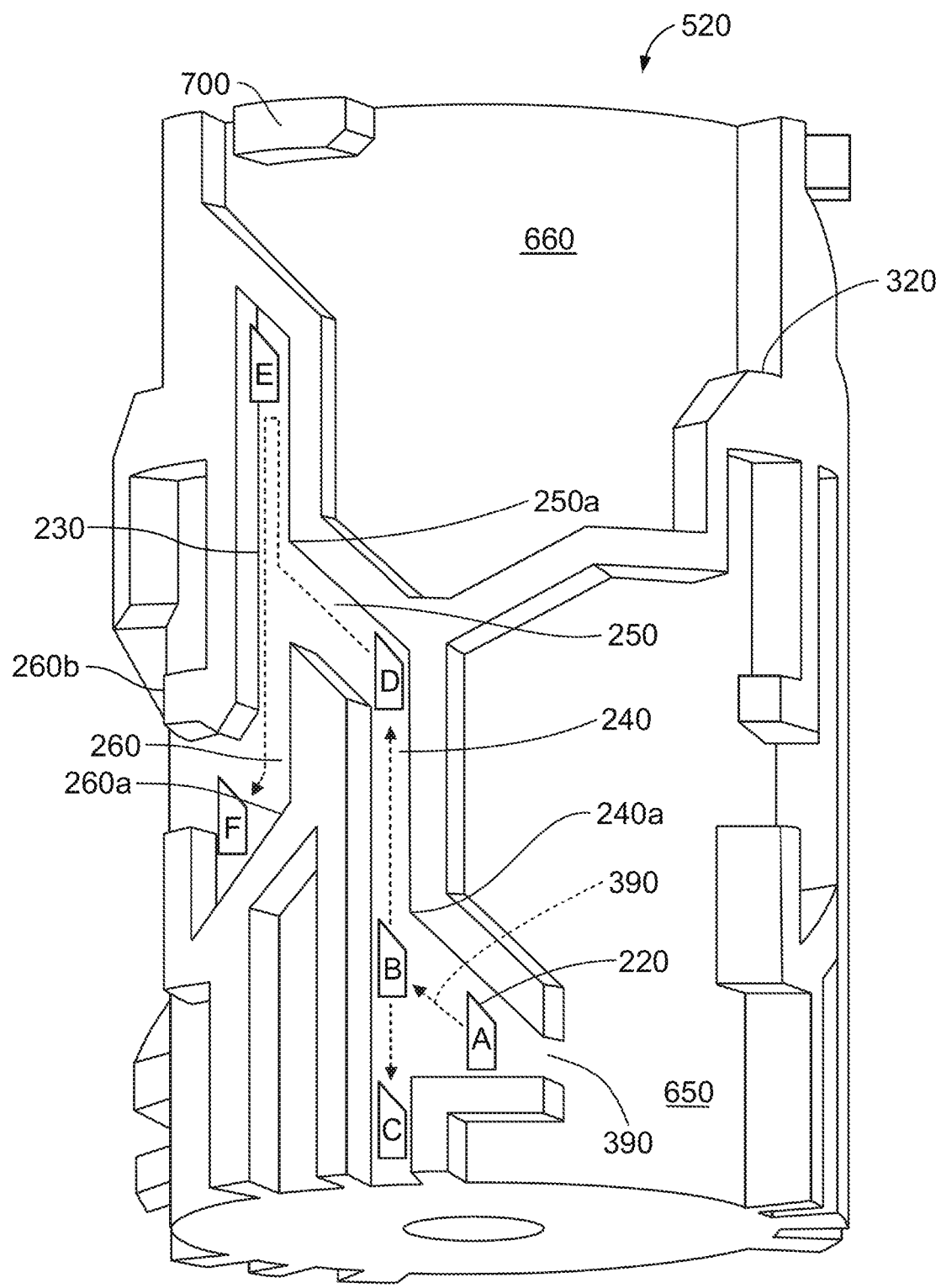
FIG. 18 is a close-up perspective view of the bypass housing of the embodiment of the needle module shown in FIG. 6 to illustrate the positions of the drive tooth during use.

FIG. 18 illustrates the travel of drive teeth 220 in one or more tracks 230 as illustrated by directional arrow 390. Drive tooth 220 begins at position A and through axial movement of the needle guard biases the bypass housing rotationally until it moves past the transition point 240a and arrives at position B. Once the drive tooth reaches position B the bypass housing and lower needle hub move proximally causing the capsule 310 to engage needles 130 and 150, and the drive tooth moves relatively to position C (this is termed as the triggering of the device) and it is the bypass housing/lower hub moving proximally under the release of stored energy that results in the effective position of the needle guard drive tooth being position C. It is important to note that the needle guard does not move under the action of the release stored energy, it is just the needle hub and the bypass housing that move relatively away from the needle guard at the point of triggering, hence the drive tooth moves from position B to position C. As the needle guard continues to retract, drive tooth 220 moves proximally in path 240 to position D, where it exerts a rotational bias on the bypass housing 520 causing it to rotate again until tooth 220 passes the transition 250a (commit point) into path 260. The drive tooth then moves proximally until position E is reached. At this point, the needle guard 420 is fully retracted and the full available insertable length of the needle is exposed. Once the user removes the guard from contact with the skin, the guard begins to extend as a result of the distal biasing force exerted by spring 480 on the inner proximal surface of the guard. The utilization of the stored energy spring to act both as a trigger/piercing spring and also, once extended post triggering, as the needle guard spring is a unique aspect of this design. It negates the need to use two separate springs for these separate functions by locating the spring in a position such that it can fulfill both roles. Initially, for example during assembly or manufacture of the medicated module, the biasing member is compressed exerting a force on the lower hub/bypass housing in preparation for triggering. Once triggered it extends proximally where upon it can then be compressed from the distal end as the needle guard retracts against it. This secondary compression provides the force to push the needle guard back to the extended and locked position as it is removed from the injection site. As the guard moves to its fully extended post-use position, which preferably is less extended than the starting position, the drive tooth 220 moves distally in path 250 until it reaches transition point 260a, where it then rotationally biases the bypass housing 520 to rotate yet again until tooth 220 enters path 260 and arrives at position F. This last rotation of bypass housing 520 causes lock out boss 700 to engage lock out feature 710. This prevents any further rotational or axial movement of the bypass housing. The needle guard is prevented from further substantial axial movement, as defined earlier, by engagement of the drive tooth with axial stop 260b. It is within the scope of our invention that a number of tooth arrangements and/or profiles could be used to fulfill the required function described above, e.g., simple equal tooth profiles or more complex multi-angled profiles. The particular profile being dependent upon the required point of commit and rotation of the bypass housing. It is also within the scope of our invention that a similar axial/rotational locking of the lower needle hub to the bypass housing as of the bypass housing to the outer housing, could be integrated to prevent movement of the needle post-triggering and post-lock out.

In any of the above described embodiments of our invention the second medicament may be either in a powdered solid state, any fluid state contained within the secondary reservoir or capsule, or coated to the inside surface of the drug dispense interface. The greater concentration of the solid form of the medicament has the benefit of occupying a smaller volume than the liquid having lower concentration. This in turn reduces the ullage of the medicated module. An additional benefit is that the solid form of the second medicament is potentially more straightforward to seal in the secondary reservoir than a liquid form of the medicament. The device would be used in the same manner as the preferred embodiment with the second medicament being dissolved by the first medicament during dispense.

To minimize diffusion of the secondary medicament contained in the capsule within the medicated module into the primary medicament during dispense of the medicaments the reservoir 222 has an integral flow distributor 232. This flow distributor also ensures efficient expulsion of the second medicament from the system and greatly minimizes residual volume. One possible embodiment of the reservoir 222 and flow distributor 232 is illustrated in FIGS. 19 and 20. Preferably the reservoir and flow distributor are manufactured as a single part from materials that are compatible with the secondary medicament, most preferably as a single molded piece. A preferred material would be that typically used to manufacture septa or pistons (bungs) found in multi-dose medicament cartridges, although any material that is compatible with the medicament during long term storage would be equally applicable. The flow distributor 232 is configured and positioned in reservoir 222 such that the secondary medicament fills flow channels that are defined by the shape and location of one or more channels (not shown) inside the reservoir. The shape of the flow channels can be optimized for a plug flow of medicament by varying the dimensions of the flow distributor and/or channels. The cross-sectional area of the annulus formed between the flow distributor and the wall of the reservoir should be kept relatively small. The volume available to store the secondary medicament would equal the internal volume of the reservoir minus the volume of the flow distributor. Therefore if the volume of the flow distributor is marginally smaller than the internal volume of the capsule, a small volume is left which the secondary medicament occupies. Hence the scale of both the capsule and the flow distributor can be large while storing a small volume of medicament. Resultantly for small volumes of secondary medicament (e.g. 50 micro liters) the reservoir can be of an acceptable size for handling, transport, manufacture, filling and assembly.

Preferably the medicated module is provided by a drug manufacturer as a stand-alone and separate device that is sealed to preserve sterility. The sterile seal of the module is preferably designed to be opened automatically, e.g. by cutting, tearing or peeling, when the medicated module is advanced or attached to the drug delivery device by the user. Features such as angled surfaces on the end of the injection device or features inside the module may assist this opening of the seal.

The medicated module of our invention should be designed to operate in conjunction with a multiple use injection device. The injection device could be a reusable or disposable device. By disposable device it is meant an injection device that is obtained from the manufacturer preloaded with medicament and cannot be reloaded with new medicament after the initial medicament is exhausted.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A drug delivery system to administer one or more medicaments operable through a delivery device and a dispense interface in the form of a medicated module, the delivery device comprising,
    a housing defining a primary reservoir, the primary reservoir containing a first medicament;
    a dose injecting mechanism operably connected to the primary reservoir containing the first medicament containing at least one drug agent;
    a triggering mechanism operably configured to the dose injecting mechanism of the delivery device;
    an outlet configured for fluid communication with the primary reservoir;
    wherein the medicated module is attachable to the drug delivery device, the medicated module comprising:
    an outer housing having an inner surface, a proximal end and a distal end, where the proximal end has an upper hub holding a first double-ended needle cannula and a connector configured for attachment to a delivery device;
    a bypass housing having an outer surface and slidably engaged with an upper radial stand off on the inner surface of the outer housing;
    a secondary reservoir within the bypass housing comprising at least a single dose of a secondary medicament;
    an activating member in the form of a guard, the guard having an internal proximal face and a drive tooth on an inner surface, where the drive tooth is slidably engaged with a track on the outer surface of the bypass housing;
    a lower hub slidably engaged with the outer surface of the bypass housing and slidably engaged with the inner surface of the guard holding a second double-ended needle cannula; and a first biasing member engaged between the internal proximal face of the guard and with the lower hub, wherein during a dose administration step, when the guard is caused to be moved in a proximal direction, the guard acts on the triggering mechanism so as to allow the dose injecting mechanism to cause the first medicament from the primary reservoir and the secondary medicament from the secondary reservoir to be expelled through the dispense interface, and allows the second double-ended needle cannula to reach a given penetration depth before the guard activates the triggering mechanism.

2. The system of claim 1 wherein the dose injecting mechanism comprises a dose setting mechanism.

3. The system of claim 1 wherein the guard comprises a lockable needle guard.

4. The drug delivery system of claim 3 the delivery device further comprising a cartridge defining the primary reservoir;

a second biasing member operatively coupled to the dose injecting mechanism;

a dose dial grip operably coupled to the dose injecting mechanism and to the second biasing member, the dose dial grip being moveable to a selected position against a bias created by the second biasing member, wherein movement of the dose dial grip to the selected position is accompanied by straining the second biasing member; and the triggering mechanism situated in part within the dose injecting mechanism and arranged to retain the dose dial grip in the selected position against the bias of the second biasing member;

wherein during the dose administration step the force for expelling being provided by the first biasing member.

5. The system of claim 4 wherein the second biasing member comprises a torsional spring.

6. The system of claim 1 wherein the delivery device comprises an automatic delivery device.

7. The system of claim 1 wherein the delivery device comprises a fixed dose delivery device.

8. The system of claim 1 wherein the delivery device comprises a multi-dose delivery device.

9. The system of claim 1 wherein the dispense interface comprises a dedicated dispense interface that can only be attached to a dedicated distal end of the delivery device, the dedicated interface comprising:

a connecting body extending from a distal end to a proximal end; and a dedicated mechanical coupling configured at the proximal end of the connecting body, wherein the dedicated mechanical coupling forms a releasable connection to the dedicated distal end of the delivery device.

10. The system of claim 9 wherein the dedicated mechanical coupling comprises a bayonet type connection that is keyed specifically to a corresponding bayonet type connection on the dedicated distal end of the delivery device.

11. The system of claim 1 wherein the primary reservoir contains one or more doses of medicament.

12. The system of claim 1 wherein said secondary medicament comprises at least one dose of a GLP-1 and a GLP-1 analog.

13. The medicated module of claim 1 wherein the secondary reservoir is a single molded component having an internal cavity with an integral flow distributor.

* * * * *